US008133695B2

(12) United States Patent
Piper et al.

(10) Patent No.: US 8,133,695 B2
(45) Date of Patent: Mar. 13, 2012

(54) FLUORESCENCE POLARIZATION HERG ASSAY

(75) Inventors: David Piper, Madison, WI (US); Kurt Vogel, Madison, WI (US); Mohammed Saleh Shekhani, Madison, WI (US); Stephen Hess, Verona, WI (US); Steve Duff, Middleton, WI (US); Thomas Livelli, Madison, WI (US); Zhong Zhong, Shanghai (CN)

(73) Assignee: Life Technologies Corporation, Carlsbad, CA (US)

( * ) Notice: Subject to any disclaimer, the term of this patent is extended or adjusted under 35 U.S.C. 154(b) by 251 days.

(21) Appl. No.: 12/394,605

(22) Filed: Feb. 27, 2009

(65) Prior Publication Data

US 2009/0253148 A1     Oct. 8, 2009

Related U.S. Application Data

(60) Provisional application No. 61/032,809, filed on Feb. 29, 2008, provisional application No. 61/032,604, filed on Feb. 29, 2008, provisional application No. 61/032,390, filed on Feb. 28, 2008.

(51) Int. Cl.
G01N 33/53 (2006.01)
G01N 33/532 (2006.01)
G01N 33/533 (2006.01)

(52) U.S. Cl. ........ 435/7.93; 435/7.1; 436/544; 436/546; 436/56

(58) Field of Classification Search ............... None
See application file for complete search history.

(56) References Cited

U.S. PATENT DOCUMENTS

| | | | |
|---|---|---|---|
| 5,206,240 A | 4/1993 | Baldwin et al. | |
| 6,458,542 B1 * | 10/2002 | George et al. | 435/6 |
| 6,838,291 B2 | 1/2005 | Liverton et al. | |
| 2004/0115814 A1 * | 6/2004 | DuBridge | 435/455 |

FOREIGN PATENT DOCUMENTS

| | | |
|---|---|---|
| EP | 0431943 | 6/1991 |
| WO | WO-2009108905 | 9/2009 |

OTHER PUBLICATIONS

International Application No. PCT/US09/35591, *International Search Report* mailed on Aug. 26, 2009, 10.
Banks et al., "Impact of a Red-Shifted Dye Label for High Throughput Fluorescence Polarization Assays of G Protein-Coupled Receptors", *Journal of Biomolecular Screening*, vol. 5, No. 5, 2000, 329-334.
Bode et al., "ICH Topic: The draft ICH S7B step 2: Note for guidance on safety pharmacology studies for human pharmaceuticals", *Fundamental & Clinical Pharmacology*, vol. 16, Issue 2, Apr. 2002, 105-118.
Bridgland-Taylor et al., "Optimisation and validation of a medium-throughput electrophysiology-based hERG assay using IonWorks™ HT", *Journal of Pharmacological and Toxicological Methods*, vol. 54, Issue 2, 2006, 189-199.
Burke et al., "Development and application of fluorescence polarization assays in drug discovery", *Comb. Chem. High Throughput Screen*, vol. 6, No. 3, May 2003, 183-194.
Cavalli et al., "Toward a pharmacophore for drugs inducing the long QT syndrome insights from a CoMFA study of Herg K(+) channel blockers", *Journal of Medicinal Chemistry*, vol. 45, No. 18, 2002, 3844-3853.
Chiu et al., "Validation of a [3H]astemizole binding assay in HEK293 cells expressing Herg K+ channels", *Journal of Pharmacology Sciences*, vol. 95, No. 3, 2004, 311-319.
Curran et al., "A Molecular Basis for Cardiac Arrhythmia: HERG Mutations Cause Long QT Syndrome", *Cell*, vol. 80, Mar. 10, 1995, 795-803.
Deacon et al., "Early evaluation of compound QT prolongation effects: A predictive 384-well fluorescence polarization binding assay for measuring hERG blockade", *Journal of Pharmacological and Toxicological Methods*, vol. 55, Issue 3, 2007, 255-264.
Diaz et al., "The [3H]dofetilide binding assay is a predictive screening tool for hERG blockade and proarrhythmia: Comparison of intact cell and membrane preparations and effects of altering $[K^+]_o$", *Journal of Pharmacological and Toxicological Methods*, vol. 50, Issue 2, 2004, 187-199.
Dubin et al., "Identifying Modulators of hERG Channel Activity Using the Patch Express® Planar Patch Clamp", *Journal of Biomolecular Screening*, vol. 10, No. 2, 2005, 168-181.
Elliot et al., "4-Oxospiro[benzopyran-2,4'-piperidines] as Class III Antiarrhythmic Agents. Pharmacological Studies on 3,4-Dihydro-1'-[2-(benzafurazan-5-yl)-ethyl]-6-methanesulfonamidospiro[(2H)-1-benzopyran-2,4'-piperdin]-4-one(L-691,121)", *Journal of Medicinal Chemistry*, vol. 35, No. 21, 1992, 3973-3976.
Finlayson et al., "[3H]dofetilide binding in SHSY5Y and HEK293 cells expressing a HERG-like K+ channel?", *European Journal of Pharmacology*, vol. 412, No. 3, 2001, 203-212.
Finlayson et al., "[3H]dofetilide binding to HERG transfected membranes: a potential high throughput preclinical screen", *European Journal of Pharmacology*, vol. 430, Issue 1, 2001, 147-148.
Gintant et al., "Utility of hERG Assays as Surrogate Markers of Delayed Cardiac Repolarization and QT Safety", *Toxicologic Pathology*, vol. 34, No. 1, Jan. 2006, 81-90.
Hamill et al., "Improved patch-clamp techniques for high-resolution current recording from cells and cell-free membrane patches", *Pfulgers Arch*, vol. 391, No. 2, 1981, 85-100.
Haverkamp et al., "The potential for QT prologation and proarrhythmia by non-antiarrhymic drugs: clinical and regulatory implications. Report on a policy conference of the European Society of Cardiology.", *European Heart Journal*, vol. 21, 2000, 1216-1231.
Huang, "Fluorescence Polarization Competition Assay: The Range of Resolvable Inhibitor Potency Is Limited By the Affinity of the Fluorescent Ligand", *Journal of Biomolecular Screening*, vol. 8, No. 1, 2003, 34-38.

(Continued)

*Primary Examiner* — Shafiqul Haq

(57) ABSTRACT

Disclosed are assays, methods, and kits for the screening of test compounds for their capability to induce cardiotoxicity in a subject. In particular, whether a test compound has the effect to prolong the Q-T interval as measured by an electrocardiogram in a human. The assays, methods, and kits disclosed herein make use of the binding interaction between novel fluorescent tracers and the hERG $K^+$ channel, and the propensity of a test compound to influence that binding interaction.

34 Claims, 7 Drawing Sheets

OTHER PUBLICATIONS

Lynch et al., "Cardiac electrophysiologic and antiarrhythmic actions of two long-acting spirobenzopyran piperidine class III agents, L-702,9958 and L-706,000 [MK-499]", *Journal of Pharamacology and Experimental Therapeutics*, vol. 269, No. 2, 1994, 541-554.

Nerenberg et al., "4-Oxospiro[benzopyran-2,4'Piperidines] as Selective Alpha 1a-Adrenergic Receptor Antagonists", *Bioorganic & Medicinal Chemistry Letters*, vol. 9, No. 2, 1999, 291-294.

Piper et al., "Development of the Predictor hERG Fluorescence Polarization Assay Using a Membrane Protein Enrichment Approach", *ASSAY and Drug Development Technologies*, vol. 6, Nov. 2, 2008, 213-223.

Raab et al., "Synthesis of the first sulfur-35-labeled hERG radioligand", *Bioorganic & Medicinal Chemistry Letters*, vol. 16, No. 6, 2006, 1692-1695.

Sanguinetti et al., "A Mechanistic Link between an Inherited and an Acquired Cardiac Arrhythmia: HERG Encodes the $I_{kr}$ Potassium Channel", *Cell*, vol. 81, Apr. 21, 1995, 299-307.

Sanguinetti et al., "hERG potassium channels and cardiac arrhythmia", *Nature*, vol. 440, Mar. 23, 2006, 463-469.

Singleton et al., "Fluorescently Labeled Analogues of Dofetilide as High-Affinity Fluorescence Polarization Ligands for the Human Ether-a-go-go-Related Gene(hERG) Channel", *Journal of Medicinal Chemistry*, vol. 50, No. 13, Jun. 28, 2007, 2931-2941.

Trudeau et al., "HERG, a Human Inward Rectifier in the Voltage-Gated Potassium Channel Family", *Science*, vol. 269, Jul. 7, 1995, 92-95.

Wang et al., "Functional and pharmacological properties of canine ERG potassium channels", *Am. J. Physiol. Heart Circ. Physiol.*, vol. 284, No. 1, 2003, H256-H267.

Warmke et al., "A family of potassium channel genes related to *eag* in Drosophila and mammals", *Proc. Natl. Acad. Sci.*, vol. 91, Apr. 1994, 3438-3442.

Whitebread et al., "Keynote review: In Vitro safety pharmacology profiling: an essential tool for successful drug development", *Drug Discovery Today*, vol. 10,.Issue 21, Nov. 2005, 1421-1433.

Wible et al., "HERG-Lite®: A novel comprehensive high-throughput screen for drug-induced hERG risk", *Journal of Pharmacological and Toxicological Methods*, vol. 52, No. 1, 2005, 136-145.

Witchel, "The hERG potassium channel as a therapeutic target", *Expert Opinion on Therapeutic Targets*, vol. 11, No. 3, 2007, 321-336.

Xavier et al., "(S)-Tetrahydro-Methyl-3,3-Diphenyl-1H,3H-Pyrrolo-[1,2-c][1,3,2]Oxazaborole-Borane Complex", *Organic Syntheses*, Coll. vol. 9, 1998, 676-686.

Zhang et al., "A Simple Statistical Parameter for Use in Evaluation and Validation of High Throughput Screening Assays", *Journal of Biomolecular Screening*, vol. 4, No. 2, 1999, 67-73.

* cited by examiner

SEQUENCE LISTING

<160> NUMBER OF SEQ ID NOS: 2

<210> SEQ ID NO 1
<211> LENGTH: 1159
<212> TYPE: PRT
<213> ORGANISM: Homo sapiens

<400> SEQUENCE: 1

```
Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Arg Lys Val Glu Ile
                85                  90                  95

Ala Phe Tyr Arg Lys Asp Gly Ser Cys Phe Leu Cys Leu Val Asp Val
                100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Ala Gly Gly Ala Gly Ala Pro Gly
                180                 185                 190

Ala Val Val Val Asp Val Asp Leu Thr Pro Ala Ala Pro Ser Ser Glu
            195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Arg His Ala Ser
    290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
        355                 360                 365
```

```
Asn Val Thr Glu Lys Val Thr Gln Val Leu Ser Leu Gly Ala Asp Val
    370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
        435                 440                 445

Cys Gln Pro Leu Ala Val Val Asp Leu Ile Val Asp Ile Met Phe Ile
    450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
                485                 490                 495

Trp Phe Leu Ile Asp Met Val Ala Ala Ile Pro Phe Asp Leu Leu Ile
            500                 505                 510

Phe Gly Ser Gly Ser Glu Glu Leu Ile Gly Leu Leu Lys Thr Ala Arg
        515                 520                 525

Leu Leu Arg Leu Val Arg Val Ala Arg Lys Leu Asp Arg Tyr Ser Glu
    530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
                565                 570                 575

Pro His Met Asp Ser Arg Ile Gly Trp Leu His Asn Leu Gly Asp Gln
            580                 585                 590

Ile Gly Lys Pro Tyr Asn Ser Ser Gly Leu Gly Gly Pro Ser Ile Lys
        595                 600                 605

Asp Lys Tyr Val Thr Ala Leu Tyr Phe Thr Phe Ser Ser Leu Thr Ser
    610                 615                 620

Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
                645                 650                 655

Gly Asn Val Ser Ala Ile Ile Gln Arg Leu Tyr Ser Gly Thr Ala Arg
            660                 665                 670

Tyr His Thr Gln Met Leu Arg Val Arg Glu Phe Ile Arg Phe His Gln
        675                 680                 685

Ile Pro Asn Pro Leu Arg Gln Arg Leu Glu Glu Tyr Phe Gln His Ala
    690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
                725                 730                 735

Leu Gln His Cys Lys Pro Phe Arg Gly Ala Thr Lys Gly Cys Leu Arg
            740                 745                 750

Ala Leu Ala Met Lys Phe Lys Thr Thr His Ala Pro Pro Gly Asp Thr
        755                 760                 765

Leu Val His Ala Gly Asp Leu Leu Thr Ala Leu Tyr Phe Ile Ser Arg
    770                 775                 780

Gly Ser Ile Glu Ile Leu Arg Gly Asp Val Val Val Ala Ile Leu Gly
```

```
              785                 790                 795                 800
Lys Asn Asp Ile Phe Gly Glu Pro Leu Asn Leu Tyr Ala Arg Pro Gly
                    805                 810                 815

Lys Ser Asn Gly Asp Val Arg Ala Leu Thr Tyr Cys Asp Leu His Lys
                    820                 825                 830

Ile His Arg Asp Asp Leu Leu Glu Val Leu Asp Met Tyr Pro Glu Phe
                    835                 840                 845

Ser Asp His Phe Trp Ser Ser Leu Glu Ile Thr Phe Asn Leu Arg Asp
                    850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                    885                 890                 895

Lys Asp Thr Glu Gln Pro Gly Glu Val Ser Ala Leu Gly Pro Gly Arg
                    900                 905                 910

Ala Gly Ala Gly Pro Ser Ser Arg Gly Arg Pro Gly Pro Trp Gly
                    915                 920                 925

Glu Ser Pro Ser Ser Gly Pro Ser Pro Glu Ser Ser Asp Glu
        930                 935                 940

Gly Pro Gly Arg Ser Ser Pro Leu Arg Leu Val Pro Phe Ser Ser
945                 950                 955                 960

Pro Arg Pro Pro Gly Glu Pro Pro Gly Gly Pro Leu Met Glu Asp
                    965                 970                 975

Cys Glu Lys Ser Ser Asp Thr Cys Asn Pro Leu Ser Gly Ala Phe Ser
                    980                 985                 990

Gly Val Ser Asn Ile Phe Ser Phe Trp Gly Asp Ser Arg Gly Arg Gln
                    995                1000                1005

Tyr Gln Glu Leu Pro Arg Cys Pro Ala Pro Thr Pro Ser Leu Leu
        1010                1015                1020

Asn Ile Pro Leu Ser Ser Pro Gly Arg Arg Pro Arg Gly Asp Val
        1025                1030                1035

Glu Ser Arg Leu Asp Ala Leu Gln Arg Gln Leu Asn Arg Leu Glu
        1040                1045                1050

Thr Arg Leu Ser Ala Asp Met Ala Thr Val Leu Gln Leu Leu Gln
        1055                1060                1065

Arg Gln Met Thr Leu Val Pro Pro Ala Tyr Ser Ala Val Thr Thr
        1070                1075                1080

Pro Gly Pro Gly Pro Thr Ser Thr Ser Pro Leu Leu Pro Val Ser
        1085                1090                1095

Pro Leu Pro Thr Leu Thr Leu Asp Ser Leu Ser Gln Val Ser Gln
        1100                1105                1110

Phe Met Ala Cys Glu Glu Leu Pro Pro Gly Ala Pro Glu Leu Pro
        1115                1120                1125

Gln Glu Gly Pro Thr Arg Arg Leu Ser Leu Pro Gly Gln Leu Gly
        1130                1135                1140

Ala Leu Thr Ser Gln Pro Leu His Arg His Gly Ser Asp Pro Gly
        1145                1150                1155

Ser

<210> SEQ ID NO 2
<211> LENGTH: 10575
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 2

| | | | | | |
|---|---|---|---|---|---|
| cgattgacat | tgattattga | ctagttatta | atagtaatca | attacggggt | cattagttca | 60 |
| tagcccatat | atggagttcc | gcgttacata | acttacggta | aatggcccgc | ctcgtgaccg | 120 |
| cccaacgacc | cccgcccatt | gacgtcaata | atgacgtatg | ttcccatagt | aacgccaata | 180 |
| gggactttcc | attgacgtca | atgggtggag | tatttacggt | aaactgccca | cttggcagta | 240 |
| catcaagtgt | atcatatgcc | aagtccgccc | cctattgacg | tcaatgacgg | taaatggccc | 300 |
| gcctggcatt | atgcccagta | catgacccta | cgggactttc | ctacttggca | gtacatctac | 360 |
| gtattagtca | tcgctattac | catggtgatg | cggttttggc | agtacaccaa | tgggcgtgga | 420 |
| tagcggtttg | actcacgggg | atttccaagt | ctccacccca | ttgacgtcaa | tgggagtttg | 480 |
| ttttggcacc | aaaatcaacg | ggactttcca | aaatgtcgta | ataaccccgc | ccgttgacg | 540 |
| caaatgggcg | gtaggcgtgt | acggtggag | gtctatataa | gcagagctcg | tttagtgaac | 600 |
| cgtcagatcg | cctggagacg | ccatccacgc | tgttttgacc | tccatagaag | acaccgggac | 660 |
| cgatccagcc | tccgcggccg | ggaacggtgc | attggaacgc | ggattccccg | tgccaagagt | 720 |
| gacgtaagta | ccgcctatag | actctatagg | cacaccccct | tggctcttat | gcatgctata | 780 |
| ctgttttttgg | cttggggcct | atacaccccc | gctccttatg | ctataggtga | tggtatagct | 840 |
| tagcctatag | gtgtgggtta | ttgaccatta | ttgaccactc | ccctattggt | gacgatactt | 900 |
| tccattacta | atccataaca | tggctctttg | ccacaactat | ctctattggc | tatatgccaa | 960 |
| tactctgtcc | ttcagagact | gacacggact | ctgtattttt | acaggatggg | gtcccattta | 1020 |
| ttatttacaa | attcacatat | acaacaacgc | cgtcccccgt | gcccgcagtt | tttattaaac | 1080 |
| atagcgtggg | atctccacgc | gaatctcggg | tacgtgttcc | ggacatgggc | tcttctccgg | 1140 |
| tagcggcgga | gcttccacat | ccgagccctg | gtcccatgcc | tccagcggct | catggtcgct | 1200 |
| cggcagctcc | ttgctcctaa | cagtggaggc | cagacttagg | cacagcacaa | tgcccaccac | 1260 |
| caccagtgtg | ccgcacaagg | ccgtggcggt | agggtatgtg | tctgaaaatg | agctcggaga | 1320 |
| ttgggctcgc | accgtgacgc | agatggaaga | cttaaggcag | cggcagaaga | agatgcaggc | 1380 |
| agctgagttg | ttgtattctg | ataagagtca | gaggtaactc | ccgttgcggt | gctgttaacg | 1440 |
| gtggagggca | gtgtagtctg | agcagtactc | gttgctgccg | cgcgcgccac | cagacataat | 1500 |
| agctgacaga | ctaacagact | gttcctttcc | atgggtcttt | tctgcagaag | cttgaattgc | 1560 |
| tcgaggctag | cgtttttaaac | ccagcacagt | ggtctagatt | cgaagaattc | atgcctgtaa | 1620 |
| gaagaggtca | cgtggctccg | caaaacacat | tcctggacac | gattataaga | agtttgagg | 1680 |
| ggcagtctag | aaagttcatc | attgcaaatg | ctcgcgtaga | gaactgcgca | gtgatctact | 1740 |
| gtaatgatgg | tttctgtgag | ctctgtggat | attcacgggc | cgaagttatg | cagcgcccat | 1800 |
| gcacatgtga | cttcctccat | ggtccccgga | cccagcggag | agctgccgct | cagattgccc | 1860 |
| aggcgttgct | gggagcagaa | gaaaggaagg | tggagatcgc | cttttaccgg | aaagatggct | 1920 |
| cctgcttcct | ctgcttggtc | gacgtagtcc | ctgtgaagaa | cgaagatggt | gctgtgataa | 1980 |
| tgttcatcct | gaatttcgag | gttgtgatgg | agaaagatat | ggtgggctca | cccgctcacg | 2040 |
| acactaacca | tcgcgggcct | cctacctctt | ggctcgcccc | agggcgggcc | aagacttta | 2100 |
| gactcaaatt | gcccgcactg | ctcgctctta | ccgcacggga | gtctagtgtc | aggagcggtg | 2160 |
| gagctggagg | cgcgggcgcc | cctggagctg | tcgtggtgga | cgtggatctc | acaccggcag | 2220 |
| cgccgtcttc | cgagagcctt | gccctggatg | aggtgaccgc | aatggacaac | cacgtggctg | 2280 |

```
gactcgggcc tgccgaggag agacgcgcct tggttggacc cgggagtcct cctcggtccg    2340
ctcccggcca acttccttcc ccgcgggctc attccctcaa ccctgatgca tctggaagct    2400
cctgttccct ggcccggact cggtcacgag agagttgtgc ttccgtacgg cgcgcttcta    2460
gcgctgatga catagaagct atgagagccg gggtgttgcc gcctcctcca cgccacgcct    2520
ccacgggtgc tatgcaccct ctgcggtccg gcctgctcaa tagcacgtcc gacagcgatc    2580
tggtgaggta tcgcactata tcaaagatcc cacaaattac attgaatttt gtcgatctca    2640 aagggatcc attcctcgct tctcccacta gcgataggga aattatcgcg cccaagatca     2700
aggagcggac tcacaacgtg accgagaagg taactcaagt tctgagcttg ggagcggatg    2760
tcctgcctga gtacaaactt caggccccga ggattcatag atggacgatt ttgcattatt    2820 ctcccttaa ggctgtttgg gactggttga tattgctgct tgtgatttac actgccgtgt     2880
ttacgccata cagcgcagct ttcctgctga aggagactga agagggacct cctgcaactg    2940
agtgtggcta cgcttgccag cccttgccg tcgtggacct gatagttgat ataatgttca     3000
ttgtagatat tctcataaat tttcggacaa cctatgtaaa tgctaacgaa gaggttgtct    3060
cccaccccgg tagaatcgcc gtccattatt ttaaaggatg gtttctcatt gatatggtgg    3120
ccgcaattcc ttttgatctc cttatctttg gatctggctc cgaggaactc atcggactgc    3180
tgaaaacagc tagactcctg cggctcgtgc gggtggcacg gaagctggac cgatactctg    3240
aatatggtgc agcggtcctc ttcttgttga tgtgtacatt cgcgctcatc gcccattggc    3300
tcgcgtgtat ttggtatgcc attggtaaca tggagcaacc ccacatggac agtagaatcg    3360
gttggctcca caatctgggc gaccagattg gcaagccgta caattcctct ggcctcggag    3420
ggccatctat caaggacaag tacgtgaccg ctctgtattt tacctttttcc tctctgacta    3480 gcgtcgggtt cggcaatgtg tctcccaata cgaactccga gaagatattc agcatttgcg    3540
tgatgttgat cggatccctc atgtatgcgt caatcttcgg caacgtgtct gcaatcattc    3600
agcgcctgta ttcagggacc gctcggtatc atacacaaat gctgagggtt agggagttca    3660
taagattcca ccaaataccc aacccactcc ggcagcgact tgaggaatat ttccagcatg    3720
cctggtccta caccaatgga atagatatga atgccgtcct caaggggttt cctgagtgct    3780
tgcaggcgga tatttgcctc catctcaacc gatccctgtt gcagcattgt aagccatta     3840 ggggtgctac taaaggctgt ctccgcgcgt tggccatgaa gttcaagacc acccacgctc    3900
cgcctggaga cactctggta cacgcaggtg atctcctcac cgccctgtac ttcatctcca    3960
ggggttccat tgaaattctc agaggggacg ttgttgtggc tattcttggt aagaatgaca    4020
tcttcgggga accactgaac ctgtatgccc ggcccgggaa aagcaacggg gacgtaagag    4080
ccctgacgta ttgtgacctg cataagatcc atagggacga cctgctcgag gtgctggata    4140
tgtacccgga gttctccgat cacttctgga gctctctgga aattacattc aacttgagag    4200
ataccaacat gatccccggg agtccaggct caaccgagct ggaaggcggc ttctctcggc    4260
agaggaagcg aaaactttca ttccgccggc gaaccgacaa ggatactgaa caaccaggag    4320
aagtgtccgc cctcggcccc ggaagagctg agcaggtcc aagttctaga ggtcgaccag     4380
gcggcccctg ggcgaatct ccatctagtg gcccatcttc cccagagtct tcagaggacg     4440
agggacccgg gcgatcttct tctccattga ggctggtgcc gtttagctca ccccggccac    4500
ctggcgagcc tcctggaggc gaaccgctta tggaggattg tgagaaatca tcagatacat    4560
gcaatccttt gtctggcgct tttagtggcg tgtccaatat cttttccttc tggggtgatt    4620
ctcggggacg acagtatcaa gaactcccca gatgcccagc cccaacgccc agtctgttga    4680
```

```
acattcctct gagttcccca ggcaggcgcc cacggggcga cgtcgagtct cgactggacg   4740
ctctccagag acaactgaat agactggaaa ctcgcctgtc agcagacatg gcaacagtgc   4800
tgcagctgct ccagagacag atgaccctgg tccctcctgc ctactccgcc gtgacgacac   4860
ctggaccagg ccccacaagc acatctcctc tgctgccagt gagtccactg ccaaccctga   4920
cactcgactc cttgagtcaa gtgagccagt ttatggcatg tgaagagctc cctcccgggg   4980
cacccgaact ccctcaagag ggacctacac ggcggctcag tcttcctggc cagctcgggg   5040
ccttgacctc caaccttttg catcgacacg gctcagaccc cggctcctga gaattccgcc   5100
ccccccctaa cgttactggc cgaagccgct tggaataagg ccggtgtgcg tttgtctata   5160
tgttattttc caccatattg ccgtcttttg gcaatgtgag ggcccggaaa cctggccctg   5220
tcttcttgac gagcattcct aggggtcttt cccctctcgc caaaggaatg caaggtctgt   5280
tgaatgtcgt gaaggaagca gttcctctgg aagcttctga agacaaacaa cgtctgtagc   5340 gacccttttgc aggcagcgga accccccacc tggcgacagg tgcctctgcg gccaaaagcc   5400
acgtgtataa gatacacctg caaaggcggc acaacccag tgccacgttg tgagttggat   5460
agttgtggaa agagtcaaat ggctctccta agcgtattca acaaggggct gaaggatgcc   5520
cagaaggtac cccatcgtat gggatctgat ctggggcctc ggtgcacatg ctttacatgt   5580
gtttagtcga ggttaaaaaa acgtctaggc ccccgaacc acgggggacgt ggttttcctt   5640 tgaaaaacac gatgataata tggccacaac catggaacaa gagacgggggg atccaccggt   5700 cgccaccatg gccttaccag tgaccgcctt gctcctgccg ctggccttgc tgctccacgc   5760
cgccaggccg agccagttcc gggtgtcgcc gctggatcgg acctggaacc tgggcgagac   5820
agtggagctg aagtgccagg tgctgctgtc caacccgacg tcgggctgct cgtggctctt   5880
ccagccgcgc ggcgccgccg ccagtcccac cttcctccta tacctctccc aaaacaagcc   5940
caaggcggcc gaggggctgg acacccagcg gttctcgggc aagaggttgg gggacacctt   6000
cgtcctcacc ctgagcgact tccgccgaga gaacgagggc tactatttct gctcggccct   6060
gagcaactcc atcatgtact tcagccactt cgtgccggtc ttcctgccag cgaagcccac   6120
cacgacgcca gcgccgcgac caccaacacc ggcgcccacc atcgcgtcgc agcccctgtc   6180
cctgcgccca gaggcgtgcc ggccagcggc gggggggcgca gtgcacacga ggggggctgga   6240 cttcgcctgt gatatctaca tctgggcgcc cttggccggg acttgtgggg tccttctcct   6300
gtcactggtt atcacccttt actgcaacca caggaaccga agacgtgttt gcaaatgtcc   6360
ccggcctgtg gtcaaatcgg gagacaagcc cagcctttcg gcgagatacg tctaaccctg   6420
tgcggccgca ggtaagccag cccaggcctc gccctccagc tcaaggcggg acaggtgccc   6480
tagagtagcc tgcatccagg acaggcccc agcgggtgc tgacacgtcc acctccatct   6540
cttcctcagg tctgcccggg tggcatccct gtgacccctc cccagtgcct ctcctggccc   6600
tggaagttgc cactccagtg cccaccagcc ttgtcctaat aaaattaagt tgcatcattt   6660
tgtctgacta ggtgtccttc tataatatta tggggtggag ggggtggta tggagcaagg   6720 ggcccaagtt aacttgttta ttgcagctta taatggttac aaataaagca atagcatcac   6780
aaatttcaca aataaagcat ttttttcact gcattctagt tgtggtttgt ccaaactcat   6840
caatgtatct tatcatgtct ggatccgctt caggcaccgg gcttgcgggt catgcaccag   6900
gtcgcgcggt ccttcgggca ctcgacgtcg gcggtgacgg tgaagccgag ccgctcgtag   6960
aaggggaggt tgcggggcgc ggaggtctcc aggaaggcgg gcaccccggc gcgctcggcc   7020
gcctccactc cggggagcac gacggcgctg cccagaccct tgccctggtg gtcgggcgag   7080
```

```
acgccgacgg tggccaggaa ccacgcgggc tccttgggcc ggtgcggcgc caggaggcct   7140
tccatctgtt gctgcgcggc cagccgggaa ccgctcaact cggccatgcg cgggccgatc   7200
tcggcgaaca ccgccccgc ttcgacgctc tccggcgtgg tccagaccgc caccgcggcg    7260
ccgtcgtccg cgacccacac cttgccgatg tcgagcccga cgcgcgtgag gaagagttct   7320
tgcagctcgg tgacccgctc gatgtggcgg tccgggtcga cggtgtggcg cgtggcgggg   7380
tagtcggcga acgcggcggc gagggtgcgt acggcccggg ggacgtcgtc gcgggtggcg   7440
aggcgcaccg tgggcttgta ctcggtcatg gtggcctgca gagtcgctcg gtgttcgagg   7500
ccacacgcgt caccttaata tgcgaagtgg acctgggacc cgccgcccc gactgcatct    7560
gcgtgttaat tcgccaatga caagacgctg ggcggggttt gtgtcatcat agaactaaag   7620
acatgcaaat atatttcttc cggggacacc gccagcaaac gcgagcaacg ggccacgggg   7680
atgaagcagc tagactcttc cgcttcctcg ctcactgact cgctgcgctc ggtcgttcgg   7740
ctgcggcgag cggtatcagc tcactcaaag gcggtaatac ggttatccac agaatcaggg   7800
gataacgcag gaaagaacat gtgagcaaaa ggccagcaaa aggccaggaa ccgtaaaaag   7860
gccgcgttgc tggcgttttt ccataggctc cgcccccctg acgagcatca caaaaatcga   7920
cgctcaagtc agaggtggcg aaacccgaca ggactataaa gataccaggc gtttccccct   7980
ggaagctccc tcgtgcgctc tcctgttccg accctgccgc ttaccggata cctgtccgcc   8040
tttctccctt cgggaagcgt ggcgctttct caatgctcac gctgtaggta tctcagttcg   8100
gtgtaggtcg ttcgctccaa gctgggctgt gtgcacgaac cccccgttca gcccgaccgc   8160
tgcgccttat ccggtaacta tcgtcttgag tccaacccgg taagacacga cttatcgcca   8220
ctggcagcag ccactggtaa caggattagc agagcgaggt atgtaggcgg tgctacagag   8280
ttcttgaagt ggtggcctaa ctacggctac actagaagga cagtatttgg tatctgcgct   8340
ctgctgaagc cagttacctt cggaaaaaga gttggtagct cttgatccgg caaacaaacc   8400
accgctggta gcggtggttt ttttgtttgc aagcagcaga ttacgcgcag aaaaaaagga   8460
tctcaagaag atcctttgat cttttctacg gggtctgacg ctcagtggaa cgaaaactca   8520
cgttaaggga ttttggtcat gagattatca aaaaggatct tcacctagat ccttttaaat   8580
taaaaatgaa gttttaaatc aatctaaagt atatatgagt aaacttggtc tgacagttac   8640
caatgcttaa tcagtgaggc acctatctca gcgatctgtc tatttcgttc atccatagtt   8700
gcctgactcc ccgtcgtgta gataactacg atacgggagg gcttaccatc tggccccagt   8760
gctgcaatga taccgcgaga cccacgctca ccggctccag atttatcagc aataaaccag   8820
ccagccggaa gggccgagcg cagaagtggt cctgcaactt tatccgcctc catccagtct   8880
attaattgtt gccgggaagc tagagtaagt agttcgccag ttaatagttt gcgcaacgtt   8940
gttgccattg ctacaggcat cgtggtgtca cgctcgtcgt ttggtatggc ttcattcagc   9000
tccggttccc aacgatcaag gcgagttaca tgatccccca tgttgtgcaa aaaagcggtt   9060
agctccttcg gtcctccgat cgttgtcaga agtaagttgg ccgcagtgtt atcactcatg   9120
gttatggcag cactgcataa ttctcttact gtcatgccat ccgtaagatg cttttctgtg   9180
actggtgagt actcaaccaa gtcattctga gaatagtgta tgcggcgacc gagttgctct   9240
tgcccggcgt caatacggga taataccgcg ccacatagca gaactttaaa agtgctcatc   9300
attggaaaac gttcttcggg gcgaaaactc tcaaggatct taccgctgtt gagatccagt   9360
tcgatgtaac ccactcgtgc acccaactga tcttcagcat cttttacttt caccagcgtt   9420
tctgggtgag caaaaacagg aaggcaaaat gccgcaaaaa agggaataag ggcgacacgg   9480
```

```
aaatgttgaa tactcatact cttctttttt caatattatt gaagcattta tcagggttat  9540
tgtctcatga gcggatacat atttgaatgt atttagaaaa ataaacaaat aggggttccg  9600
cgcacatttc cccgaaaagt gccacctgac gtctaagaaa ccattattat catgacatta  9660
acctataaaa ataggcgtat cacgaggccc ctttcgtctc gcgcgtttcg gtgatgacgg  9720
tgaaaacctc tgacacatgc agctcccgga gacggtcaca gcttgtctgt aagcggatgc  9780
cgggagcaga caagcccgtc agggcgcgtc agcgggtgtt ggcgggtgtc ggggctggct  9840
taactatgcg gcatcagagc agattgtact gagagtgcac catatgcggt gtgaaatacc  9900
gcacagatgc gtaaggagaa aataccgcat caggaaattg taaacgttaa tattttgtta  9960
aaattcgcgt taaattttg ttaaatcagc tcatttttta accaataggc cgaaatcggc  10020
aaatcccctt ataaatcaaa agaatagacc gagatagggt tgagtgttgt tccagtttgg  10080
aacaagagtc cactattaaa gaacgtggac tccaacgtca aagggcgaaa aaccgtctat  10140
cagggcgatg gcccactacg tgaaccatca ccctaatcaa gttttttggg gtcgaggtgc  10200
cgtaaagcac taaatcggaa ccctaaaggg agcccccgat ttagagcttg acggggaaag  10260
ccggcgaacg tggcgagaaa ggaagggaag aaagcgaaag gagcgggcgc tagggcgctg  10320
gcaagtgtag cggtcacgct gcgcgtaacc accacaccg ccgcgcttaa tgcgccgcta  10380
cagggcgcgt cgcgccattc gccattcagg ctacgcaact gttgggaagg gcgatcggtg  10440
cgggcctctt cgctattacg ccagctggcg aaggggggat gtgctgcaag gcgattaagt  10500
tgggtaacgc cagggttttc ccagtcacga cgttgtaaaa cgacggccag tgaattgtcg  10560
aggtctcgac ggtat                                                  10575
```

FLUORESCENCE POLARIZATION HERG ASSAY

CROSS REFERENCE TO RELATED APPLICATIONS

This application claims the benefit under 35 U.S.C. §119 (e) of U.S. Provisional Patent Application No. 61/032,390, filed Feb. 28, 2008, U.S. Provisional Patent Application No. 61/032,604, filed Feb. 29, 2008, and U.S. Provisional Patent Application No. 61/032,809, filed Feb. 29, 2008, the disclosures of which are hereby incorporated herein by reference in their entirety.

FIELD OF THE INVENTION

The present invention relates to the field of cardiovascular safety assays, in particular to assays, methods, and kits for the screening of test compounds for their capability to induce cardiotoxicity in a subject. The assays, methods, and kits disclosed herein are based on the interaction of novel fluorescent tracer compounds with the hERG $K^+$ channel, which interaction is exploited by means of membrane preparations from a cell line engineered to have a high level of hERG $K^+$ channel expression. The assays, methods, and kits disclosed herein may be useful to identify compounds with undesirable effects on cardiac repolarization in man, in particular the propensity to prolong the Q-T interval in an electrocardiogram.

BACKGROUND OF THE INVENTION

The human ether-a-go-go related gene (hERG) encodes the rapidly delayed inward rectifying potassium channel ($I_{Kr}$) that profoundly effects the repolarization of the human ventricle (see, Curran, M. E.; Splawski, I.; Timothy, K. W.; Vincent, G. M.; Green, E. D.; Keating, M. T., A molecular basis for cardiac arrhythmia: HERG mutations cause long QT syndrome. *Cell* 1995, 80, (5), 795-803; Sanguinetti, M. C.; Jiang, C.; Curran, M. E.; Keating, M. T., A mechanistic link between an inherited and an acquired cardiac arrhythmia: HERG encodes the IKr potassium channel. *Cell* 1995, 81, (2), 299-307; Trudeau, M. C.; Warmke, J. W.; Ganetzky, B.; Robertson, G. A., HERG, a human inward rectifier in the voltage-gated potassium channel family. *Science* 1995, 269, (5220), 92-5; and Warmke, J. W.; Ganetzky, B., A family of potassium channel genes related to eag in Drosophila and mammals. *Proc Natl Acad Sci USA* 1994, 91, (8), 3438-42). Block of IK, repolarizing current flowing through the channel in ventricular muscle can result in prolongation of the Q-T interval, a characteristic electrocardiogram pattern termed torsades de pointes, and potentially lethal arrhythmia (see, Sanguinetti, M. C.; Tristani-Firouzi, M., hERG potassium channels and cardiac arrhythmia. *Nature* 2006, 440, (7083), 463-9; and Haverkamp, W.; Breithardt, G.; Camm, A. J.; Janse, M. J.; Rosen, M. R.; Antzelevitch, C.; Escande, D.; Franz, M.; Malik, M.; Moss, A.; Shah, R., The potential for QT prolongation and proarrhythmia by non-antiarrhythmic drugs: clinical and regulatory implications. Report on a policy conference of the European Society of Cardiology. *Eur Heart J* 2000, 21, (15), 1216-31). The promiscuous nature of this channel, referred to herein as the hERG $K^+$ channel, to bind a diverse set of chemical structures (see, Cavalli, A.; Poluzzi, E.; De Ponti, F.; Recanatini, M., Toward a pharmacophore for drugs inducing the long QT syndrome: insights from a CoMFA study of HERG K(+) channel blockers. *J Med Chem* 2002, 45, (18), 3844-53), coupled with the potential fatal outcome that may emerge from that interaction, have resulted in the recommendation from the International Congress of Harmonization and the U.S. Food and Drug Administration that all new drug candidates undergo testing in a functional patch-clamp assay using the human hERG protein, either in native form or expressed in recombinant form (see, Bode, G.; Olejniczak, K., ICH topic: the draft ICH S7B step 2: note for guidance on safety pharmacology studies for human pharmaceuticals. *Fundam Clin Pharmacol* 2002, 16, (2), 105-18). Although automated, high-throughput patch-clamp methods have been recently developed, such systems require specialized operators, live cells, and a substantial capital investment (see, Bridgland-Taylor, M. H.; Hargreaves, A. C.; Easter, A.; Orme, A.; Henthorn, D. C.; Ding, M.; Davis, A. M.; Small, B. G.; Heapy, C. G.; Abi-Gerges, N.; Persson, F.; Jacobson, I.; Sullivan, M.; Albertson, N.; Hammond, T. G.; Sullivan, E.; Valentin, J. P.; Pollard, C. E., Optimisation and validation of a medium-throughput electrophysiology-based hERG assay using IonWorks HT. *J Pharmacol Toxicol Methods* 2006, 54, (2), 189-99; and Dubin, A. E.; Nasser, N.; Rohrbacher, J.; Hermans, A. N.; Marrannes, R.; Grantham, C.; Van Rossem, K.; Cik, M.; Chaplan, S. R.; Gallacher, D.; Xu, J.; Guia, A.; Byrne, N. G.; Mathes, C., Identifying modulators of hERG channel activity using the PatchXpress planar patch clamp. *J Biomol Screen* 2005, 10, (2), 168-81). Further, since patch-clamp testing is costly, and because numerous, chemically-diverse scaffolds block the hERG $K^+$ channel, strategies to mitigate potential cardiac liability during early-stage drug development typically employ a binding assay to predict the ability of a compound to block hERG current in the functional patch-clamp assay (see, Whitebread, S.; Hamon, J.; Bojanic, D.; Urban, L., Keynote review: in vitro safety pharmacology profiling: an essential tool for successful drug development. *Drug Discov Today* 2005, 10, (21), 1421-33; and Diaz, G. J.; Daniell, K.; Leitza, S. T.; Martin, R. L.; Su, Z.; McDermott, J. S.; Cox, B. F.; Gintant, G. A., The [3H]dofetilide binding assay is a predictive screening tool for hERG blockade and proarrhythmia: Comparison of intact cell and membrane preparations and effects of altering [K+]o. *J Pharmacol Toxicol Methods* 2004, 50, (3), 187-99).

Radioligand binding assays that use [$^3$H]-dofetilide (see, Diaz, G. J.; Daniell, K.; Leitza, S. T.; Martin, R. L.; Su, Z.; McDermott, J. S.; Cox, B. F.; Gintant, G. A., The [3H]dofetilide binding assay is a predictive screening tool for hERG blockade and proarrhythmia: Comparison of intact cell and membrane preparations and effects of altering [K+]o. *J Pharmacol Toxicol Methods* 2004, 50, (3), 187-99; and Finlayson, K.; Turnbull, L.; January, C. T.; Sharkey, J.; Kelly, J. S., [3H]dofetilide binding to HERG transfected membranes: a potential high throughput preclinical screen. *Eur J Pharmacol* 2001, 430, (1), 147-8), [$^3$H]-astemizole (see, Chiu, P. J.; Marcoe, K. F.; Bounds, S. E.; Lin, C. H.; Feng, J. J.; Lin, A.; Cheng, F. C.; Crumb, W. J.; Mitchell, R., Validation of a [3H]astemizole binding assay in HEK293 cells expressing HERG $K^+$ channels. *J Pharmacol Sci* 2004, 95, (3), 311-9), or [$^{35}$S]-MK499 (see, Wang, J.; Della Penna, K.; Wang, H.; Karczewski, J.; Connolly, T. M.; Koblan, K. S.; Bennett, P. B.; Salata, J. J., Functional and pharmacological properties of canine ERG potassium channels. *Am J Physiol Heart Circ Physiol* 2003, 284, (1), H256-67) have been shown to be predictive of hERG $K^+$ channel block. However, the preparation, storage, and disposal of the radioligands adds time and cost to the assay procedure. Additionally, the radiometric assays that have been described to assess compound binding to the hERG $K^+$ channel are heterogeneous filter binding assays, and require a separation of free from bound radioligand by capturing radioligand-bound membrane protein on filter paper using a vacuum manifold. This procedure makes the assay difficult to automate for large-scale screening or routine compound profiling, thereby limiting its practical utility. Additionally, over the past decade, there has been a strong push within both industry and academia to develop non-radioactive methods to replace such assays.

Fluorescence polarization (FP) assays provide a fully homogenous, mix-and-read format to characterize the affinity of a ligand for a receptor, and in many cases can be used to replace many radiometric binding assays (see, Burke, T. J.; Loniello, K. R.; Beebe, J. A.; Ervin, K. M., Development and application of fluorescence polarization assays in drug discovery. *Comb Chem High Throughput Screen* 2003, 6, (3), 183-94). The technique is based on the ability of a compound to displace a fluorescent probe (a "tracer") from a receptor, which is detected by a change in an optical signal. In such an assay, the tracer typically consists of a known, high-affinity ligand for the receptor that has been chemically attached to a fluorescent molecule, without substantially disrupting the affinity of the receptor-ligand interaction (see, Huang, X., Fluorescence polarization competition assay: the range of resolvable inhibitor potency is limited by the affinity of the fluorescent ligand. *J Biomol Screen* 2003, 8, (1), 34-8). When a tracer molecule is excited with plane-polarized light in an FP assay, the polarization of the emitted light is retained if the fluorophore maintains its orientation during the time (typically nanoseconds) between photon excitation and emission. In solution, this orientation is largely maintained when the tracer is bound to a larger molecule, such as a protein, because the protein-tracer complex rotates more slowly than the free tracer itself. When the tracer is displaced from the receptor by a ligand that binds to the receptor, emission of light from the tracer is depolarized relative to the excitation source.

An important practical distinction between a traditional radioligand binding assay and an FP assay is that, in contrast to a radioligand binding assay, FP assays are optimally configured using a limiting amount of tracer, and a concentration of receptor that is at or above the $K_d$ value for the receptor-tracer interaction. This is because the optical signal that is measured is dependant on the signal from all of the tracer that is present—both free and bound, which is unlike that in a radioligand binding assay in which (after separation) the only signal measured is due to bound ligand, and free ligand does not contribute to the signal. Thus, in an FP assay, any unbound tracer contributes to the amount of depolarized light present, thereby lowering the polarization signal that is measured, and lowering the assay window. Typically, FP assays are configured such that between 50 and 70% of the total tracer is bound in the absence of competing ligand in order to strike a balance between the assay window (maximal—minimal polarization values that are measured) and the assay sensitivity (ability of $IC_{50}$ values to approach true $K_i$ values) (see, Huang, X., Fluorescence polarization competition assay: the range of resolvable inhibitor potency is limited by the affinity of the fluorescent ligand. *J Biomol Screen* 2003, 8, (1), 34-8). When developing FP assays using purified, soluble, recombinant proteins, this is typically not an issue because many such proteins are readily prepared in quantities sufficient for such assays. However, this requirement can pose a challenge when developing assays for membrane-associated proteins, such as hERG, which in most cases have not been purified in functional form from their membrane components, which include both insoluble lipid components as well as other proteins. Moreover, the presence of large amounts of membrane components can interfere with the assay by scattering light (see, Banks, P.; Gosselin, M.; Prystay, L., Impact of a red-shifted dye label for high throughput fluorescence polarization assays of G protein-coupled receptors. *J Biomol Screen* 2000, 5, (5), 329-34) or by leading to increased non-specific binding of the tracer (which often contains a lipophilic fluorophore) with the membrane itself.

Accordingly, the development of a homogenous, FP-based assay to identify and characterize the affinity of small molecules for the hERG $K^+$ channel, and demonstrate tight correlation with data obtained from either radioligand binding or patch-clamp assays, has heretofore not been realized.

SUMMARY OF THE INVENTION

In order to avoid the issues associated with radiometric assays to assess hERG $K^+$ channel binding, a homogenous, FP-based substitute for these assays has been developed. A traditional radioligand displacement assay was used initially to identify candidate high-affinity fluorescent tracers. However, because the level of hERG $K^+$ channel expression ($B_{max}$) in the initial cell line was insufficient to configure an FP assay, a strategy was developed to increase hERG $K^+$ channel expression levels by coupling the expression of a cell-surface marker (CD8) to the expression of hERG $K^+$ channel, using a bicistronic expression vector that encoded both proteins. This strategy allowed for the clonal isolation of high-expressing hERG $K^+$ channel cell lines using flow cytometry, and enabled the development of the FP assay, including further tracer development and assay optimization. The resulting FP assay is predictive of hERG $K^+$ channel binding, is simple to perform using standard plate readers, and is well suited to replace traditional radiometric binding assays as a means of triaging compounds for hERG $K^+$ channel liability.

Described herein are FP assays, methods, and kits for the screening of small molecules, i.e., test compounds, to characterize their affinity for the hERG $K^+$ channel, and their capability to induce cardiotoxicity in a subject. In addition, described herein are processes for preparing novel fluorescent tracer compounds and membrane preparations having a high level of hERG $K^+$ channel expression for use in the disclosed assays, methods, and kits.

One aspect of the present invention provides a novel fluorescent tracer compound having the general structural formula (I):

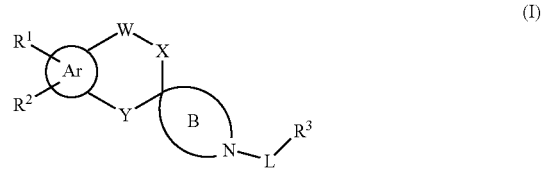

or a pharmaceutically acceptable salt thereof,
wherein:
Ar is an aromatic ring selected from the group consisting of benzo, thieno, furo, and pyrido;
$R^1$ and $R^2$ are independently selected from the group consisting of:
  1) hydrogen,
  2) $C_{1-6}$ alkyl, either unsubstituted or substituted with
    a) —$NR^4R^5$, wherein $R^4$ and $R^5$ are independently hydrogen or $C_{1-6}$ alkyl,
    b) —$N(R^5)COC_{1-6}$ alkyl,
    c) —$NHSO_2(C_{1-6}$ alkyl),
    d) —$CONR^6R^7$, wherein $R^6$ and $R^7$ are independently i) hydrogen,
ii) $C_{1-6}$ alkyl, or
iii) $R^6$ and $R^7$ taken together with the nitrogen atom to which they are attached represent a 5- or 6-membered saturated heterocyclic ring, which may contain an additional heteroatom selected from N, $S(O)_n$, or O, selected from the group consisting of pyrrolidine, morpholine, piperidine, piperazine, and N-methylpiperazine,
e) —CO($C_{1-6}$ alkyl),
f) —OH,
g) —O($C_{1-6}$ alkyl),
h) —O($C_{1-6}$ alkyl)-O—($C_{1-3}$ alkyl),
i) —S(O)$_n$($C_{1-6}$ alkyl),
j) imidazole,
k) 2-imidazolidinone,
l) 2-pyrrolidinone,
m) —NH—C(NHR$^5$)=N—CN, or
n) —NH—C(SR$^5$)=N—CN,
3) —OH,
4) $C_{1-3}$ alkoxy, either unsubstituted or substituted with $C_{1-3}$ alkoxy,
5) —N(R$^5$)SO$_2$($C_{1-6}$ alkyl),
6) —N(R$^5$)SO$_2$(CH$_2$)$_g$CO$_2$H, wherein g is 1-5,
7) —N(R$^5$)SO$_2$(CH$_2$)$_g$CO$_2$C$_{1-6}$ alkyl,
8) —NO$_2$,
9) —N(R$^5$)COC$_{1-6}$ alkyl,
10) —N(R$^5$)SO$_2$—C$_6$H$_4$—R$^4$,
11) —N(R$^5$)CO—C$_6$H$_4$—R$^4$,
12) —NR$^4$R$^5$,
13) halo,
14) —CO—C$_{1-6}$ alkyl,
15) —CONR$^6$R$^7$,
16) —CN,
17) —CO$_2$R$^5$,
18) —C(R$^5$)=N—OR$^8$,
19) benzoyl, either unsubstituted or substituted with $C_{1-6}$ alkyl, $C_{1-6}$ alkoxy, halo, or hydroxy,
20) —N(R$^5$)COO($C_{1-6}$ alkyl),
21) —N(R$^5$)COO-phenyl, either unsubstituted or substituted with $C_{1-6}$ alkyl, $C_{1-6}$ alkoxy, hydroxy or halo,
22) —N(R$^5$)CONR$^4$R$^5$,
23) —S(O)$_n$C$_{1-6}$ alkyl,
24) —S(O)$_n$—C$_6$H$_4$—R$^4$,
25) —CF$_3$,
26) phenyl, either unsubstituted or substituted with $C_{1-6}$ alkyl, $C_{1-6}$ alkoxy, halo or hydroxy,
27) imidazolyl,
28) —SO$_2$NR$^6$R$^7$,
29) —N[S(O)$_2$C$_{1-6}$alkyl][(CH$_2$)$_p$CN], wherein p is 2-5,
30) —N(R$^5$)—C(NR$^4$R$^5$)=N—CN, and
31) —N(R$^5$)—C(SR$^5$)=N—CN;
the ring system comprising W, X, and Y is a 5-, 6-, or 7-membered ring system wherein W, X, and Y are independently —O—, C=O, —(CR$^4$R$^5$)$_n$—, C=NOR$^8$, CHOR$^9$, —NR$^9$—, CHNR$^{10}$R$^{11}$, —S(O)$_n$—, =CH—, =N—, or a bond; wherein:
R$^4$ and R$^5$ are as defined above,
R$^8$ is
a) hydrogen, or
b) $C_{1-6}$ alkyl, unsubstituted or substituted with —COOR$^5$;
R$^9$ is
a) hydrogen,
b) $C_{1-6}$ alkyl,
c) (CH$_2$)$_n$—C$_6$H$_4$—R$^2$, wherein R$^{12}$ is
i) —NO$_2$,
ii) $C_{1-3}$ alkyl,
iii) —O—C$_{1-3}$ alkyl,
iv) halo,
v) —CF$_3$, or
vi) hydrogen,
d) —CO—C$_{1-6}$ alkyl,
e) —CO—C$_6$H$_4$—R$^{12}$,
f) —COO—C$_{1-6}$ alkyl, or
g) —CONR$^4$R$^5$;
R$^{10}$ and R$^{11}$ are independently
a) hydrogen,
b) $C_{1-6}$ alkyl, unsubstituted or substituted with —(CR$^4$R$^5$)$_n$—(CR$^4$R$^5$)$_g$—R$^{13}$, wherein g is 1-5, and R$^{13}$ is
i) hydrogen,
ii) —OH, or
iii) —OC$_{1-6}$ alkyl,
c) —CO—C$_{1-6}$ alkyl, unsubstituted or substituted with
i) —OH,
ii) —N(R$^4$R$^5$),
iii) —OC$_{1-6}$ alkyl, or
iv) —CO$_2$R$^5$,
d) —CO—C$_6$H$_4$—R$^{13}$, or
e) R$^{10}$ and R$^{11}$ taken together with the nitrogen atom to which they are attached represent a 5- or 6-membered saturated heterocyclic ring, unsubstituted or substituted with oxygen or hydroxy, which may contain an additional heteroatom selected from N, S(O), or O, selected from the group consisting of pyrrolidine, morpholine, piperidine, pyrrolidinone, piperidinone, piperazine and N-methylpiperazine;
n is 0, 1, or 2;
B is a 5- to 7-membered N-containing ring;
L is —(CR$^4$R$^5$)$_m$-Q—(CR$^4$R$^5$)$_q$—NH—[CZ—(CR$^4$R$^5$)$_u$-(D)$_w$]$_z$—, wherein
R$^4$ and R$^5$ are as defined above,
m and q are independently 1 to about 5,
u is 0 to about 7,
w is 0 or 1,
z is 1 or 2,
Q is a bond, —O—, C=O, CHOH, —NR$^5$— or —S(O)$_n$—,
Z is =O or =S, and
D is —O—, —S(O)$_n$—, —NR$^5$—, or —NR$^5$SO$_2$—; and
R$^3$ is a fluorescent dye.

Another aspect of the present invention provides an assay for screening test compounds, wherein the assay is a binding assay using a fluorescent tracer described herein binding to a source of the hERG K$^+$ channel or fragment thereof.

Another aspect of the present invention provides a method for characterizing the activity of a test compound as a hERG K$^+$ channel blocker, the method comprising the steps of:

a) contacting the test compound with a membrane preparation containing a hERG K$^+$ channel having the amino acid sequence of SEQ ID NO: 1, the membrane preparation derived from cells transfected with a nucleic acid expression vector including a nucleotide sequence which encodes the hERG K$^+$ channel, in an assay buffer in the presence of a fluorescent tracer described herein;

b) monitoring whether the test compound influences the binding of the fluorescent tracer to the membrane preparation containing the hERG K$^+$ channel; and c) determining the hERG K$^+$ channel blocker activity of the test compound.

Another aspect of the present invention provides a kit for screening test compounds, the kit comprising:

a) a fluorescent tracer described herein;
b) a source of the hERG K$^+$ channel or fragment thereof; and
c) an assay buffer.

Another aspect of the present invention provides a hERG K+ channel-expressing cell population, wherein the cell population expresses at least about 100 pmol of hERG K+ channel per mg of total membrane protein.

Another aspect of the present invention provides a process for preparing a fluorescent tracer compound of structural formula (I)

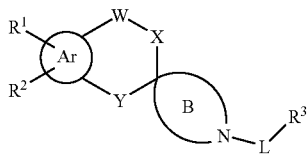

the process comprising:
a) reacting a compound of structural formula (II)

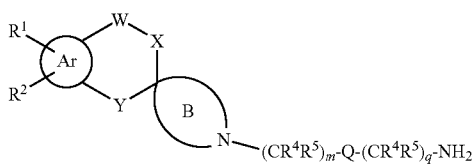

in dimethylformamide/diisopropylethyl amine at room temperature with a compound of structural formula (III)

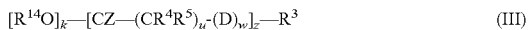

wherein:
$R^1$, $R^2$, $R^3$, $R^4$, $R^5$, Ar, B, D, L, Q, W, X Y, Z, m, q, u, w, and z are as defined above; k is 0 or 1; and
$R^{14}$ is a component of an active ester;
provided that if Z is =O, then k is 1, and
provided that if Z is =S, then k is 0, u is 0, w is 1, z is 1, and D is =N.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Definitions

Figure 1:
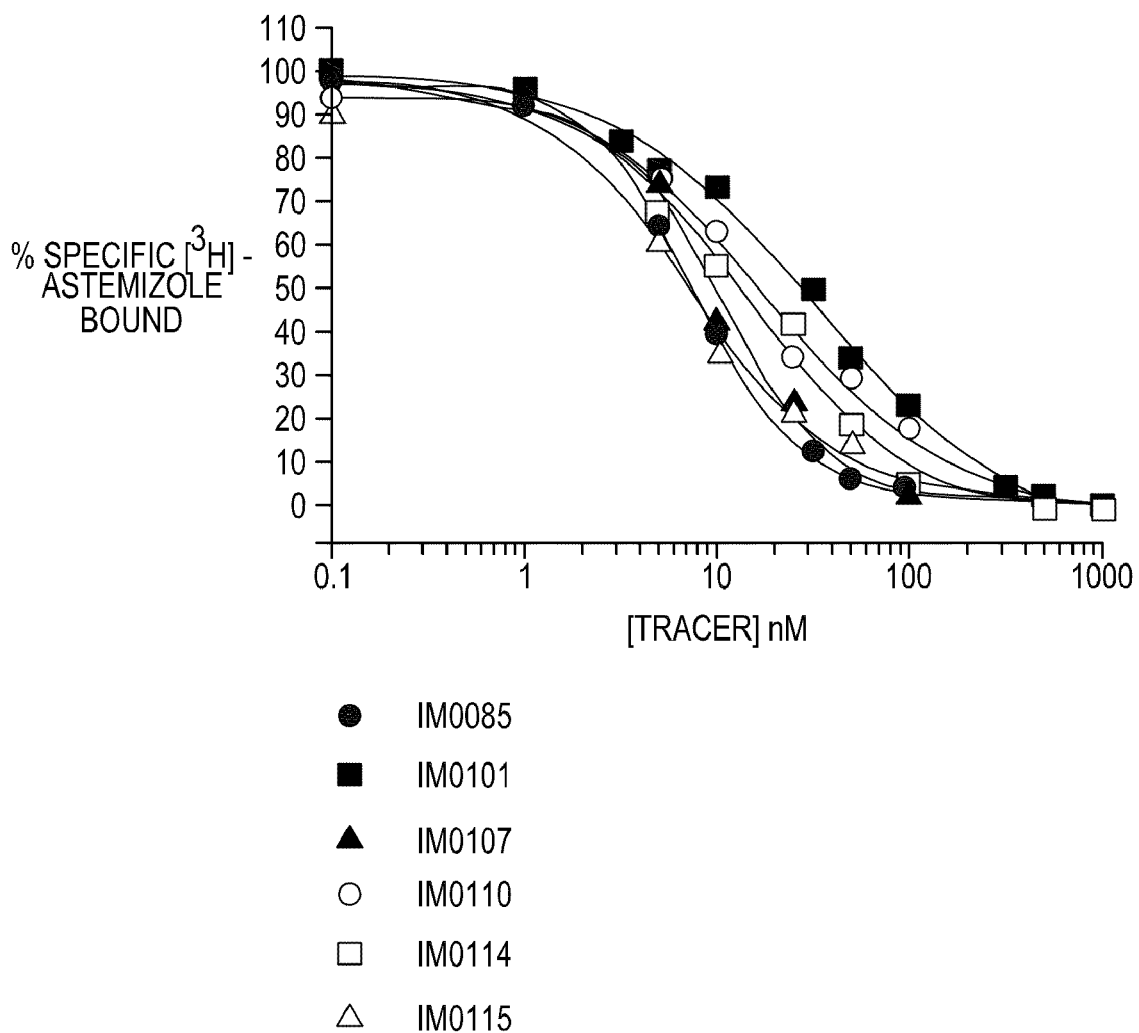
FIG. 1 shows six candidate fluorescent tracers (identified by their internal compound identification numbers) initially evaluated for hERG K+ channel affinity as determined by a radioligand displacement assay that displaced [³H]-astemizole with an IC$_{50}$ value of less than 30 nM.
Figure 2A:
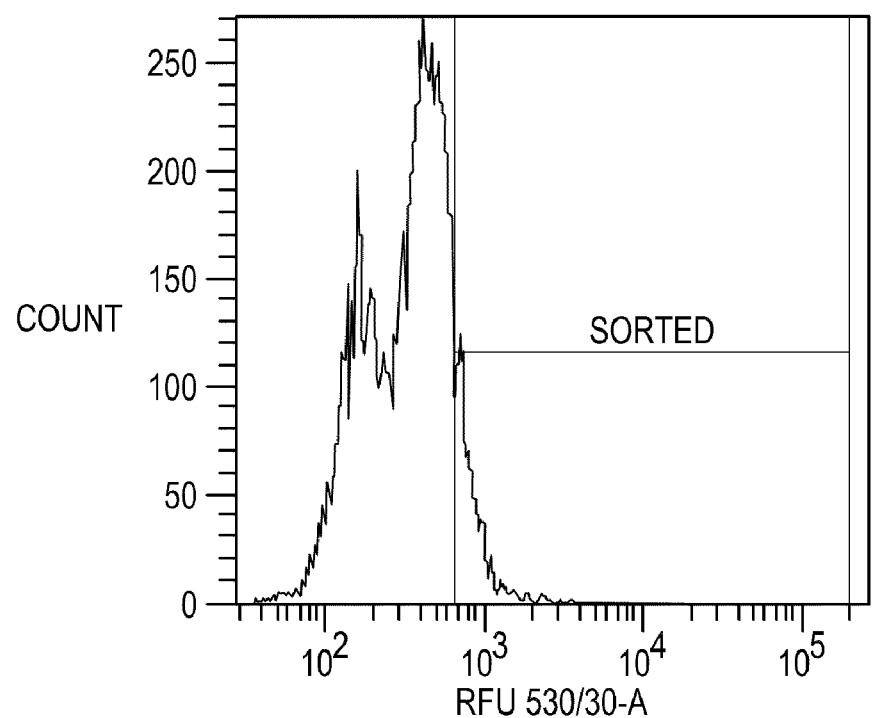
FIG. 2 shows clonal isolation of high-expressing hERG K+ channel cell line: (A) The top 10% of CD8+ cells were isolated by FACS. (B) 192 single cells were expanded and analyzed by immunocytochemistry for CD8 expression. (C) Six clones were analyzed by manual patch clamp, and peak tail current recorded. "T-REx" refers to the original inducible hERG cell line analyzed and "Pool" refers to the original sort of high-CD8-expressing cells. (D) A membrane preparation from clone D was analyzed by radioligand binding. (○) total bound ligand (●) specific bound ligand, (x) non-specific bound ligand.
Figure 2B:
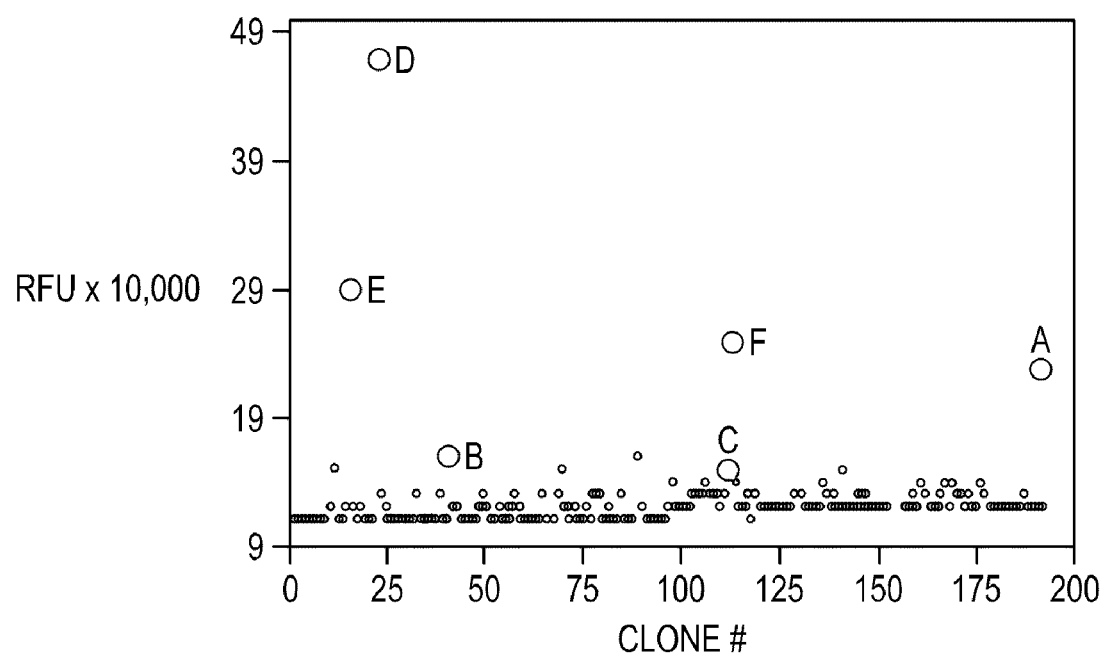
Figure 2C:
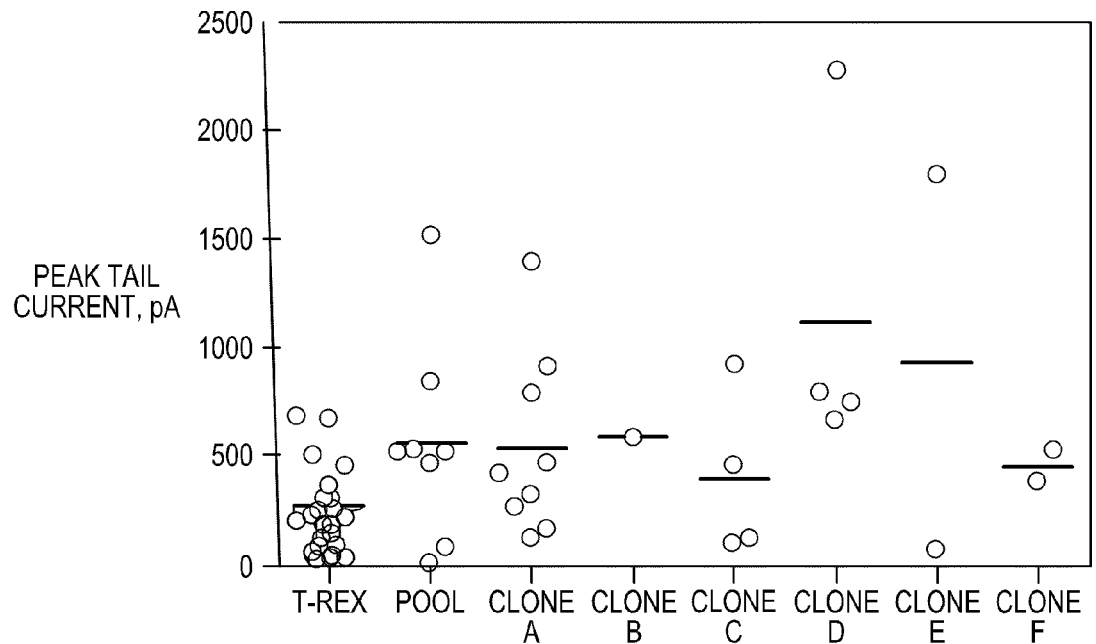
Figure 2D:
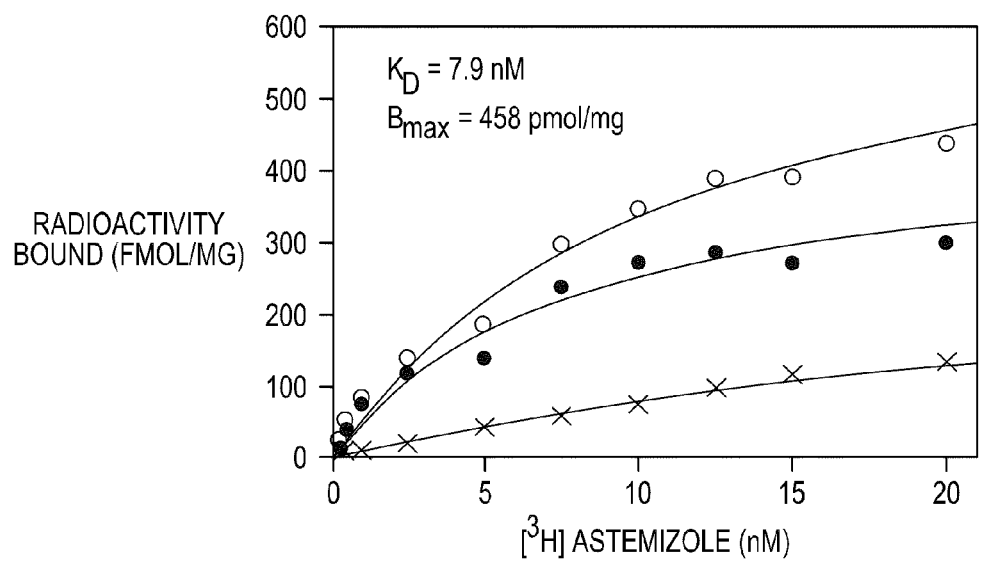

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise.

Unless defined otherwise, all technical and scientific terms used herein have the same meaning as commonly understood by one of ordinary skill in the art to which this invention is related. The following terms are defined for purposes of the invention as described herein:

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" or "Ar" refers to a monovalent aromatic carbocyclic group of from 5 to 14 carbon atoms having a single ring (e.g., benzo) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom.

"Amino" refers to the group —NH$_2$.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Carboxyl" or "carboxy" refers to —COOH or salts thereof.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties.

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Spirocyclyl" or "spiro" refers to divalent saturated cyclic group from 3 to 10 carbon atoms having a cycloalkyl or heterocyclyl ring with a spiro union (the union formed by a single atom which is the only common member of the rings).

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

The term "dye" as used herein refers to a compound that emits light to produce an observable detectable signal.

The term "fluorophore" or "fluorogenic" as used herein refers to a composition that demonstrates a change in fluorescence upon binding to a biological compound or analyte of interest. Preferred fluorophores of the present invention include fluorescent dyes having a high quantum yield in aqueous media. Exemplary fluorophores include xanthene, indole, borapolyazaindacene, furan, and benzofuran, among others. The fluorophores of the present invention may be substituted to alter the solubility, spectral properties or physical properties of the fluorophore.

The term "linker" as used herein, refers to a series of stable covalent bonds incorporating atoms selected from the group consisting of C, N, O, and S that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like.

The term "BSA" as used herein refers to bovine serum albumin.

The term "CMV" as used herein refers to cytomegalovirus.

The term "D-MEM" as used herein refers to Dulbecco's Modified Eagle Medium.

The term "DMSO" as used herein refers to dimethyl sulfoxide.

The term "EDTA" as used herein refers to ethylenediamine tetraacetic acid.

The term "FACS" as used herein refers to fluorescence automated cell sorting.

The term "FBS" as used herein refers to fetal bovine serum.

The term "FP" as used herein refers to fluorescence polarization.

The term "HEPES" as used herein refers to 4-(2-hydroxyethyl)-1-piperazineethanesulfonic acid.

The term "hERG" as used herein refers to the human ether-a-go-go related gene.

The term "LQTS" as used herein refers to long Q-T syndrome.

The term "MEM NEAA" as used herein refers to minimal essential medium with non-essential amino acids.

The term "PBS" as used herein refers to phosphate buffered saline.

The term "TdP" as used herein refers to Torsades de Pointe.

Particular Aspects of the Invention:

Development of an FP assay to assess hERG K$^+$ channel binding required that a series of fluorescent tracer compounds be synthesized with varying scaffolds, substituents, linkers and fluorophores (see, Singleton, D. H.; Boyd, H.; Steidl-Nichols, J. V.; Deacon, M.; Groot, M. J.; Price, D.; Nettleton, D. O.; Wallace, N. K.; Troutman, M. D.; Williams, C.; Boyd, J. G., Fluorescently Labeled Analogues of Dofetilide as High-Affinity Fluorescence Polarization Ligands for the Human Ether-a-go-go-Related Gene (hERG) Channel. *J Med Chem* 2007, 50, (13), 2931-2941). Accordingly, one aspect of the present invention provides a novel fluorescent tracer compound having the general structural formula (I):

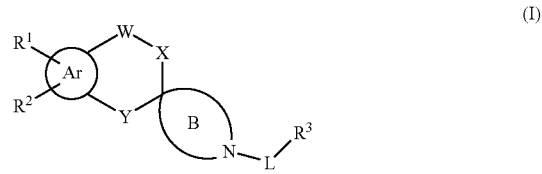

or a pharmaceutically acceptable salt thereof,
wherein:
Ar is an aromatic ring selected from the group consisting of benzo, thieno, furo, and pyrido;
$R^1$ and $R^2$ are independently selected from the group consisting of:
1) hydrogen,
2) $C_{1-6}$ alkyl, either unsubstituted or substituted with
  a) —NR$^4$R$^5$, wherein R$^4$ and R$^5$ are independently hydrogen or $C_{1-6}$ alkyl,
  b) —N(R$^5$)COC$_{1-6}$ alkyl,
  c) —NHSO$_2$(C$_{1-6}$ alkyl),
  d) —CONR$^6$R$^7$, wherein R$^6$ and R$^7$ are independently
    i) hydrogen,
    ii) $C_{1-6}$ alkyl, or iii) $R^6$ and $R^7$ taken together with the nitrogen atom to which they are attached represent a 5- or 6-membered saturated heterocyclic ring, which may contain an additional heteroatom selected from N, $S(O)_n$, or O, selected from the group consisting of pyrrolidine, morpholine, piperidine, piperazine, and N-methylpiperazine,
   e) —CO($C_{1-6}$ alkyl),
   f) —OH,
   g) —O($C_{1-6}$ alkyl),
   h) —O($C_{1-6}$ alkyl)-O—($C_{1-3}$ alkyl),
   i) —$S(O)_n$($C_{1-6}$ alkyl),
   j) imidazole,
   k) 2-imidazolidinone,
   l) 2-pyrrolidinone,
   m) —NH—C(NHR$^5$)=N—CN, or
   n) —NH—C(SR$^5$)=N—CN,
3) —OH,
4) $C_{1-3}$ alkoxy, either unsubstituted or substituted with $C_{1-3}$ alkoxy,
5) —N($R^5$)$SO_2$($C_{1-6}$ alkyl),
6) —N($R^5$)$SO_2$($CH_2$)$_g$$CO_2$H, wherein g is 1-5,
7) —N($R^5$)S $O_2$($CH_2$)$_g$$CO_2$$C_{1-6}$ alkyl,
8) —$NO_2$,
9) —N($R^5$)CO$C_{1-6}$ alkyl,
10) —N($R^5$)$SO_2$—$C_6H_4$—$R^4$,
11) —N($R^5$)CO—$C_6H_4$—$R^4$,
12) —NR$^4$R$^5$,
13) halo,
14) —CO—$C_{1-6}$ alkyl,
15) —CONR$^6$R$^7$,
16) —CN,
17) —$CO_2$R$^5$,
18) —C(R$^5$)=N—OR$^8$,
19) benzoyl, either unsubstituted or substituted with $C_{1-6}$ alkyl, $C_{1-6}$ alkoxy, halo, or hydroxy,
20) —N($R^5$)COO($C_{1-6}$ alkyl),
21) —N($R^5$)COO-phenyl, either unsubstituted or substituted with $C_{1-6}$ alkyl, $C_{1-6}$ alkoxy, hydroxy or halo,
22) —N($R^5$)CONR$^4$R$^5$,
23) —$S(O)_n$$C_{1-6}$ alkyl,
24) —$S(O)_n$—$C_6H_4$—$R^4$,
25) —$CF_3$,
26) phenyl, either unsubstituted or substituted with $C_{1-6}$ alkyl, $C_{1-6}$ alkoxy, halo or hydroxy,
27) imidazolyl,
28) —$SO_2$NR$^6$R$^7$,
29) —N[S(O)$_2$$C_{1-6}$alkyl][($CH_2$)$_p$CN], wherein p is 2-5,
30) —N($R^5$)—C(NR$^4$R$^5$)=N—CN, and
31) —N($R^5$)—C(SR$^5$)=N—CN;
the ring system comprising W, X, and Y is a 5-, 6-, or 7-membered ring system wherein W, X, and Y are independently —O—, C=O, —(CR$^4$R$^5$)$_n$—, C=NOR$^8$, CHOR$^9$, —NR$^9$—, CHNR$^{10}$R$^{11}$, —$S(O)_n$—, =CH—, =N—, or a bond; wherein:
   $R^4$ and $R^5$ are as defined above,
   $R^8$ is
   a) hydrogen, or
   b) $C_{1-6}$ alkyl, unsubstituted or substituted with —COOR$^5$;
   $R^9$ is
   a) hydrogen,
   b) $C_{1-6}$ alkyl,
   c) ($CH_2$)$_n$—$C_6H_4$—$R^{12}$, wherein $R^{12}$ is
      i) —$NO_2$,
      ii) $C_{1-3}$ alkyl,
      iii) —O—$C_{1-3}$ alkyl,
      iv) halo,
      v) —$CF_3$, or
      vi) hydrogen,
   d) —CO—$C_{1-6}$ alkyl,
   e) —CO—$C_6H_4$—$R^{12}$,
   f) —COO—$C_{1-6}$ alkyl, or
   g) —CONR$^4$R$^5$;
$R^{10}$ and $R^{11}$ are independently
   a) hydrogen,
   b) $C_{1-6}$ alkyl, unsubstituted or substituted with —(CR$^4$R$^5$)$_n$—(CR$^4$R$^5$)$_g$—R$^{13}$, wherein g is 1-5, and $R^{13}$ is
      i) hydrogen,
      ii) —OH, or
      iii) —O$C_{1-6}$ alkyl,
   c) —CO—$C_{1-6}$ alkyl, unsubstituted or substituted with
      i) —OH,
      ii) —N(R$^4$R$^5$),
      iii) —O$C_{1-6}$ alkyl, or
      iv) —$CO_2$R$^5$,
   d) —CO—$C_6H_4$—R$^{13}$, or
   e) $R^{10}$ and $R^{11}$ taken together with the nitrogen atom to which they are attached represent a 5- or 6-membered saturated heterocyclic ring, unsubstituted or substituted with oxygen or hydroxy, which may contain an additional heteroatom selected from N, $S(O)_n$ or O, selected from the group consisting of pyrrolidine, morpholine, piperidine, pyrrolidinone, piperidinone, piperazine and N-methylpiperazine;
n is 0, 1, or 2;
B is a 5- to 7-membered N-containing ring;
L is —(CR$^4$R$^5$)$_m$-Q-(CR$^4$R$^5$)$_q$—NH—[CZ—(CR$^4$R$^5$)$_u$-(D)$_w$]$_z$—, wherein
   $R^4$ and $R^5$ are as defined above,
   m and q are independently 1 to about 5,
   u is 0 to about 7,
   w is 0 or 1,
   z is 1 or 2,
   Q is a bond, —O—, C=O, CHOH, —NR$^5$— or —$S(O)_n$—,
   Z is =O or =S, and
   D is —O—, —$S(O)_n$—, —NR$^5$—, or —NR$^5$$SO_2$—; and
$R^3$ is a fluorescent dye.

Despite recognition that a subset of the aforemetnioned fluorescent tracers exhibited high-affinity binding for the hERG K$^+$ channel (FIG. 1), a finding suggesting that at least one such fluorescent tracer might prove useful for assay development, standard hERG K$^+$ channel-containing membranes were insufficient to enable a robust FP assay. Specifically, the highest affinity fluorescent tracers were examined for their utility in an FP assay using membrane preparations derived from the hERG-T-REx™ 293 cell line. These initial experiments failed to exhibit a measurable difference in fluorescence polarization in the presence or absence of known hERG K$^+$ channel blockers such as E-4031 or dofetilide. These results were not surprising as a robust FP assay requires both a high affinity tracer and protein concentrations sufficient to bind ~50% or more of the tracer in the absence of displacing compounds (see, Huang, X., Fluorescence polarization competition assay: the range of resolvable inhibitor potency is limited by the affinity of the fluorescent ligand. *J Biomol Screen* 2003, 8, (1), 34-8).

Accordingly, another aspect of the present invention provides for increasing the specific activity ($B_{max}$) of hERG K$^+$ channel membrane preparations. Since the $B_{max}$ levels required to configure an FP assay are well above those typically described for cell lines used in radioligand binding and patch-clamp assays, increasing the specific activity ($B_{max}$) of hERG K$^+$ channel membrane preparations was no less important than identifying fluorescent tracer candidates with sufficient affinity. To accomplish the former objective, an expression vector (SEQ ID NO: 2) was constructed using a CMV promoter to drive transcription of a bicistronic element composed of nucleotide sequences encoding the hERG K+ channel and the CD8 cell surface marker, wherein translation of the two proteins was linked by an internal ribosomal entry site sequence (IRES). A puromycin-resistance marker was included on the expression vector to provide a means of selecting cells wherein stable, genomic incorporation of the expression cassette had occurred. In one illustrative variation, the expression vector includes a nucleotide sequence encoding a hERG K+ channel having the amino acid sequence of SEQ ID NO: 1. In another illustrative variation, the expression vector may include a nucleotide sequence encoding a hERG K+ channel having an amino acid sequence that is at least 80% homologous to that of SEQ ID NO: 1.

Following transfection and isolation of high-expressing cells by two successive rounds of FACS, single cell clone expansion, and immunocytochemical staining, a hERG K+ channel-expressing cell population with a $B_{max}$ of greater than 450 pmol of hERG K+ channel per mg of total membrane protein was obtained. Further, the underlying methodology enables the production of hERG K+ channel-expressing cell populations with $B_{max}$ values over a broad range, i.e., preferably at least about 100 pmol to greater than 450 pmol of hERG K+ channel per mg of total membrane protein, more preferably about 200 pmol to greater than about 450 pmol of hERG K+ channel per mg of total membrane protein, even more preferably about 300 pmol to greater than about 450 pmol of hERG K+ channel per mg of total membrane protein, and most preferably a $B_{max}$ of greater than 450 pmol of hERG K+ channel per mg of total membrane protein.

Another aspect of the present invention provides a process for preparing a fluorescent tracer compound of structural formula (I)

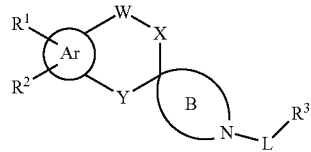

the process comprising:
a) reacting a compound of structural formula (II)

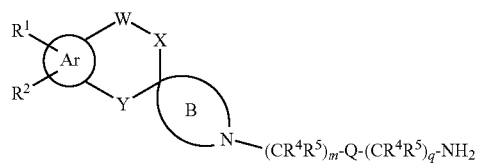

in dimethylformamide/diisopropylethyl amine at room temperature with a compound of structural formula (III)

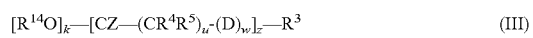

wherein:
$R^1$, $R^2$, $R^3$, $R^4$, $R^5$, Ar, B, D, L, Q, W, X Y, Z, m, q, u, w, and z are as defined above;
k is 0 or 1; and
$R^{14}$ is a component of an active ester;

provided that if Z is =O, then k is 1, and
provided that if Z is =S, then k is 0, u is 0, w is 1, z is 1, and D is =N.

In one illustrative embodiment, compound (III) is a carboxylic acid succinimidyl ester, such that $R^{14}$ is succinimidyl. In another illustrative embodiment, compound (III) is a carboxylic acid 4-sulfo-2,3,5,6-tetrafluorophenyl ester, such that $R^{14}$ is 4-sulfo-2,3,5,6-tetrafluorophenyl. In yet another illustrative embodiment, compound (III) is an isothiocyanate.

Another aspect of the present invention provides an assay for screening test compounds, wherein the assay is a binding assay using a fluorescent tracer described herein binding to a source of the hERG K+ channel or fragment thereof. Illustratively, the assay includes the steps of:
a) incubating the fluorescent tracer or salt thereof with the source of the hERG K+ channel or fragment thereof in an assay buffer in the presence or absence of different amounts of a test compound or a mixture of test compounds; and
b) measuring an effect of the test compound or the mixture of test compounds on the amount of the fluorescent tracer bound to the hERG K+ channel or fragment thereof.

In an illustrative embodiment, the assay buffer comprises 15 mM to 50 mM HEPES, 5 mM to 20 mM KCl, 0.5 mM to 2 mM $MgCl_2$, and 0.02% to about 0.1% PLURONIC F-127, and the source of the hERG K+ channel or fragment thereof is selected from the group consisting of:
i) membrane preparations derived from cells expressing on the surface thereof the hERG K+ channel of fragment thereof;
ii) cells expressing on the surface thereof the hERG K+ channel of fragment thereof; and
iii) membrane preparations derived from tissue expressing on the surface thereof the hERG K+ channel of fragment thereof.

In a preferred embodiment, the source of the hERG K+ channel or fragment thereof are membrane preparations derived from cells expressing on the surface thereof the hERG K+ channel or fragment thereof, and the assay buffer comprises 25 mM HEPES, 15 mM KCl, 1 mM $MgCl_2$, and 0.05% PLURONIC F-127, wherein the pH of the assay buffer is between pH 7.2 and pH 7.6 at room temperature. In a most preferred embodiment, the cells express greater than about 450 pmol of hERG K+ channel per mg of total membrane protein, and the assay buffer is at pH 7.4.

Another aspect of the present invention provides a method for characterizing the activity of a test compound as a hERG K+ channel blocker. Illustratively, the method includes the steps of:
a) contacting the test compound with a membrane preparation containing a hERG K+ channel having the amino acid sequence of SEQ ID NO: 1, the membrane preparation derived from cells transfected with a nucleic acid expression vector including a nucleotide sequence which encodes the hERG K+ channel, in an assay buffer in the presence of a fluorescent tracer described herein;
b) monitoring whether the test compound influences the binding of the fluorescent tracer to the membrane preparation containing the hERG K+ channel; and
c) determining the hERG K+ channel blocker activity of the test compound.

In an illustrative embodiment, the nucleic acid expression vector further includes a nucleotide sequence which encodes an internal ribosomal entry site protein and a nucleotide sequence which encodes CD-8 plasma membrane protein, wherein the nucleotide sequences which encode the internal ribosomal entry site protein and the CD-8 plasma membrane protein are located successively downstream from the nucleotide sequence which encodes the hERG K+ channel. In another illustrative embodiment, the nucleic acid expression vector has the nucleotide sequence of SEQ ID NO: 2, and monitoring whether the test compound influences the binding of the fluorescent tracer to the membrane preparation containing the hERG K+ channel is measured by fluorescence polarization. In a preferred embodiment, the assay buffer is at pH 7.4 and comprises 25 mM HEPES, 15 mM KCl, 1 mM $MgCl_2$, and 0.05% PLURONIC F-127, and expression of the hERG K+ channel is coupled to expression of the CD-8 plasma protein by means of the nucleotide sequence which encodes an internal ribosomal entry site protein.

Another aspect of the present invention provides a kit for screening test compounds. Illustratively, the kit includes:

a) a fluorescent tracer described herein;

b) a source of the hERG K+ channel or fragment thereof; and c) an assay buffer.

In a preferred embodiment, the source of the hERG K+ channel or fragment thereof are membrane preparations derived from cells expressing on the surface thereof the hERG K+ channel or fragment thereof, wherein the cells express at least about 100 pmol of hERG K+ channel per mg of total membrane protein, and the assay buffer includes 25 mM HEPES, 15 mM KCl, 1 mM $MgCl_2$, and 0.05% PLURONIC F-127 at pH 7.4.

A detailed description of the invention having been provided above, the following examples are given for the purpose of illustrating the invention and shall not be construed as being a limitation on the scope of the invention or claims.

EXAMPLES

Chemical Syntheses

Preparation of Linker (4)

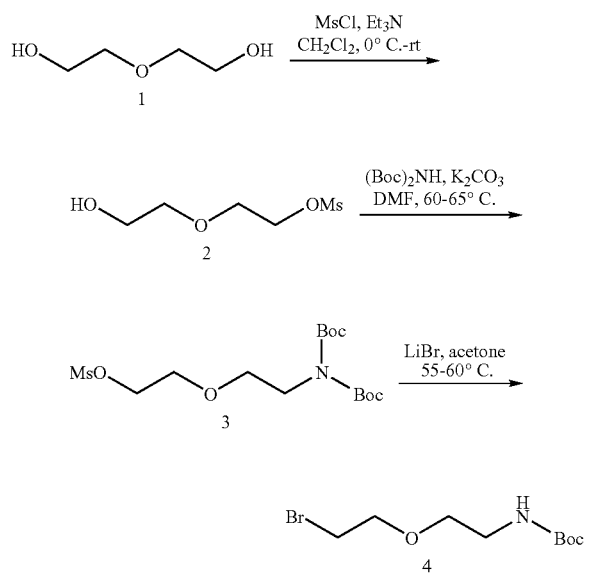

2,2'-Oxybis(ethane-2,1-diyl) dimethanesulfonate (2)

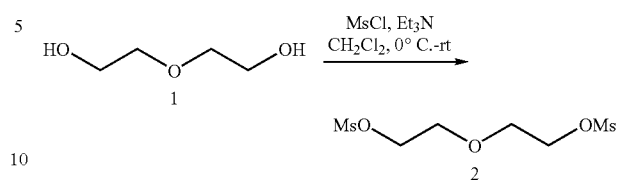

Diethylene glycol (1, 5.0 mL, 53 mmol) and triethylamine ($Et_3N$, 16.2 mL, 116 mmol) were dissolved in 40 mL of dichloromethane in a 100 mL 3-neck round bottom flask equipped with a 10 mL addition funnel, a thermometer, an argon inlet, and a magnetic stir bar. The solution was cooled to 0-5° C. in an ice bath. Methanesulfonyl chloride (MsCl, 8.4 mL, 108 mmol) was added dropwise, via the addition funnel, at a rate so as to keep the reaction solution below 15° C. The ice bath was removed and the reaction was stirred at ambient temperature overnight (~16 hours). Water (25 mL) was added and the mixture was stirred until the solids dissolved. The layers were separated and the organic (lower) layer was washed successively with two 20 mL portions of ice cold 3M hydrochloric acid, 25 mL of 5% aqueous sodium carbonate, and 25 mL of saturated aqueous sodium chloride. The organic phase (lower) was dried over anhydrous sodium sulfate, filtered, and evaporated to dryness on a rotary evaporator to provide 13 g of orange solid.

This material was purified by flash chromatography on 150 g of Silica Gel 60 (230-400 mesh), eluting with 1:1 ethyl acetate-toluene and collecting ~125 mL fractions. Based on TLC (silica gel, 4:1 ethyl acetate-toluene, ceric ammonium molybdate visualization; $R_f(1)$=0.05–0.3, $R_f(2)$=0.46–0.64), fractions were combined and concentrated to a slurry by rotary evaporation under reduced pressure. The slurry was cooled in an ice bath and the solid was collected by vacuum filtration, washed with ice-cold toluene, and dried in vacuo at 25° C. to afford 2,2'-oxybis(ethane-2,1-diyl) dimethanesulfonate (2) as a white solid (11.79 g, 85% yield) that was homogeneous by TLC. $^1$H NMR (300 MHz, $CDCl_3$): δ 3.0 (s, 6H), δ 3.8 (m, 4H), and δ 4.4 (m, 4H).

2-(2-(bis(tert-Butoxycarbonyl)amino)ethoxy)ethyl methanesulfonate (3)

2,2'-Oxybis(ethane-2,1-diyl) dimethanesulfonate (2, 10 g, 38 mmol), potassium carbonate powder (5.3 g, 38 mmol), and di-tert-butyl iminodicarboxylate (9.1 g, 42 mmol) were dissolved in 25 mL of anhydrous DMF in a 100 mL round bottom flask. This mixture was stirred at 60-65° C. for ~3 hours. An additional 10 mL of anhydrous DMF was added and stirring at 60-65° C. was continued. After ~24 h, TLC (silica gel, 1:1 ethyl acetate-toluene, ceric ammonium molybdate visualization; $R_f(2)=0.3-0.4$, $R_f(3)=0.6-0.7$) still showed starting material (2), so stirring at 60-65° C. was continued. After an additional ~24 hours, TLC showed no further change, so the reaction was cooled to room temperature. Water (30 mL) and ethyl acetate (60 mL) were added and the mixture was transferred to a separatory funnel. The layers were separated and the aqueous (lower) layer was extracted with ethyl acetate. The ethyl acetate extracts were combined and washed successively with 25 mL of 1 M aqueous hydrochloric acid, two 25 mL portions of water, and 25 mL of saturated aqueous sodium chloride. The ethyl acetate solution was dried over anhydrous sodium sulfate, filtered, and concentrated under reduced pressure on a rotary evaporator followed by high vacuum to afford 13.72 g of very pale yellow oil.

This material was purified by flash chromatography on 260 g of Silica Gel 60 (230-400 mesh), eluting successively with 15:85 ethyl acetate-hexanes, 25:75 ethyl acetate-hexanes, and 30:70 ethyl acetate-hexanes, collecting ~125 mL fractions. Based on TLC (silica gel, 15:85 ethyl acetate-hexanes, ceric ammonium molybdate visualization), fractions were combined and concentrated by rotary evaporation under reduced pressure to give 7.21 g of clear, colorless oil. This material was still not homogeneous by TLC (silica gel, 1:1 ethyl acetate-hexanes, ceric ammonium molybdate visualization; $R_f(2)=0.08-0.2$, $R_f(3)=0.65-0.75$ with minor impurities at $R_f=0.45-0.5$ and $R_f=0.55-0.65$) so it was purified again by flash chromatography on 150 g of Silica Gel 60 (230-400 mesh), eluting with 20:80 ethyl acetate-hexanes and collecting ~125 mL fractions. Based on TLC (silica gel, 1:1 ethyl acetate-hexanes, ceric ammonium molybdate visualization), fractions were combined and concentrated followed by high vacuum to afford 2-(2-(bis(tert-butoxycarbonyl)amino)ethoxy)ethyl methanesulfonate (3) as a clear, colorless oil (4.58 g, 31% yield). TLC (silica gel, 1:1 ethyl acetate-hexanes, ceric ammonium molybdate visualization) shows 3 at $R_f=0.65-0.75$ with a trace impurity at $R_f=0.45-0.5$. $^1$H NMR (300 MHz, CDCl$_3$): δ 1.5 (s, 18H), δ 3.1 (s, 3H), and δ 3.5-3.9 (m)+δ 4.3 (m)=8H.

tert-Butyl 2-(2-bromoethoxy)ethylcarbamate (4)

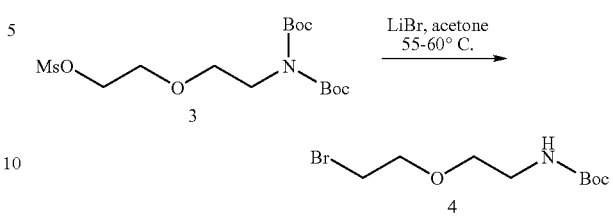

Lithium bromide (7.6 g, 87 mmol) was added to a solution of compound 3 (3.35 g, 8.74 mmol) in 33 mL of acetone and heated in an oil bath at 55-60° C. After 3 hours TLC (1:1 ethyl acetate-hexanes, ceric ammonium molybdate visualization) showed complete disappearance of starting material (3, $R_f=0.7-0.8$) and appearance of a major new product (4, $R_f=0.8-0.9$). The reaction mixture was cooled to room temperature and water (~15 mL) was added. The resulting solution was extracted twice with 25 mL portions of ethyl acetate. The combined ethyl acetate extract was washed with water (15 mL), dried over anhydrous sodium sulfate, filtered, and concentrated by rotary evaporation under reduced pressure to give a clear, colorless oil (2.05 g).

This material was purified by flash chromatography on 60 g of Silica Gel 60 (230-400 mesh) eluting with 15:85 ethyl acetate-hexanes and collecting ~50 mL fractions. Based on TLC (silica gel, 50:50 ethyl acetate-hexanes, ceric ammonium molybdate visualization), fractions were combined and concentrated under reduced pressure on a rotary evaporator followed by high vacuum to afford tert-butyl 2-(2-bromoethoxy)ethylcarbamate (4) as a clear, colorless oil (1.92 g, 82% yield) that was homogenous by TLC. Mass spec: m/z=268.4 (100%), 270.2 (93%) [M+H]$^+$
$^1$H NMR (300 MHz, CDCl$_3$): δ 1.4 (s, 9H), δ 3.2-3.8 (m, 8H), and δ 4.9 (br s, 1H).

Preparation of Spiropiperidine Ketone Linked to Dye (13)

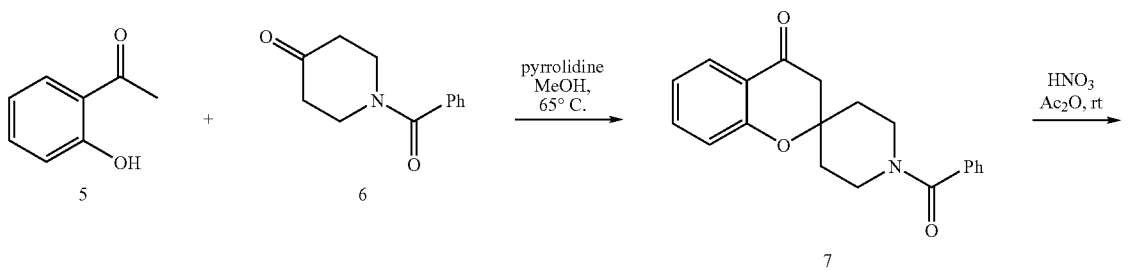

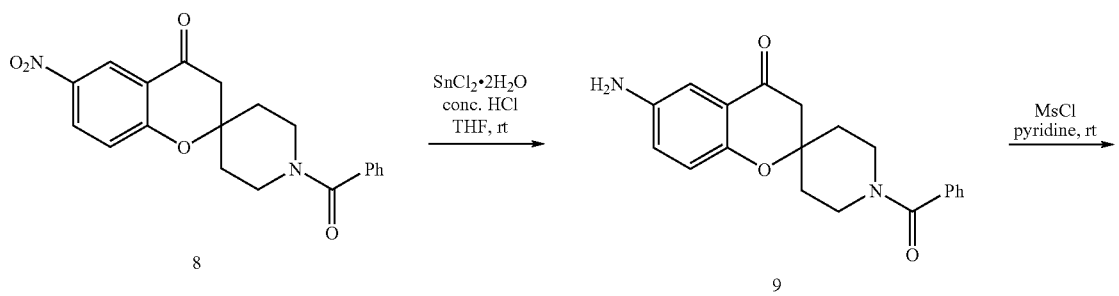

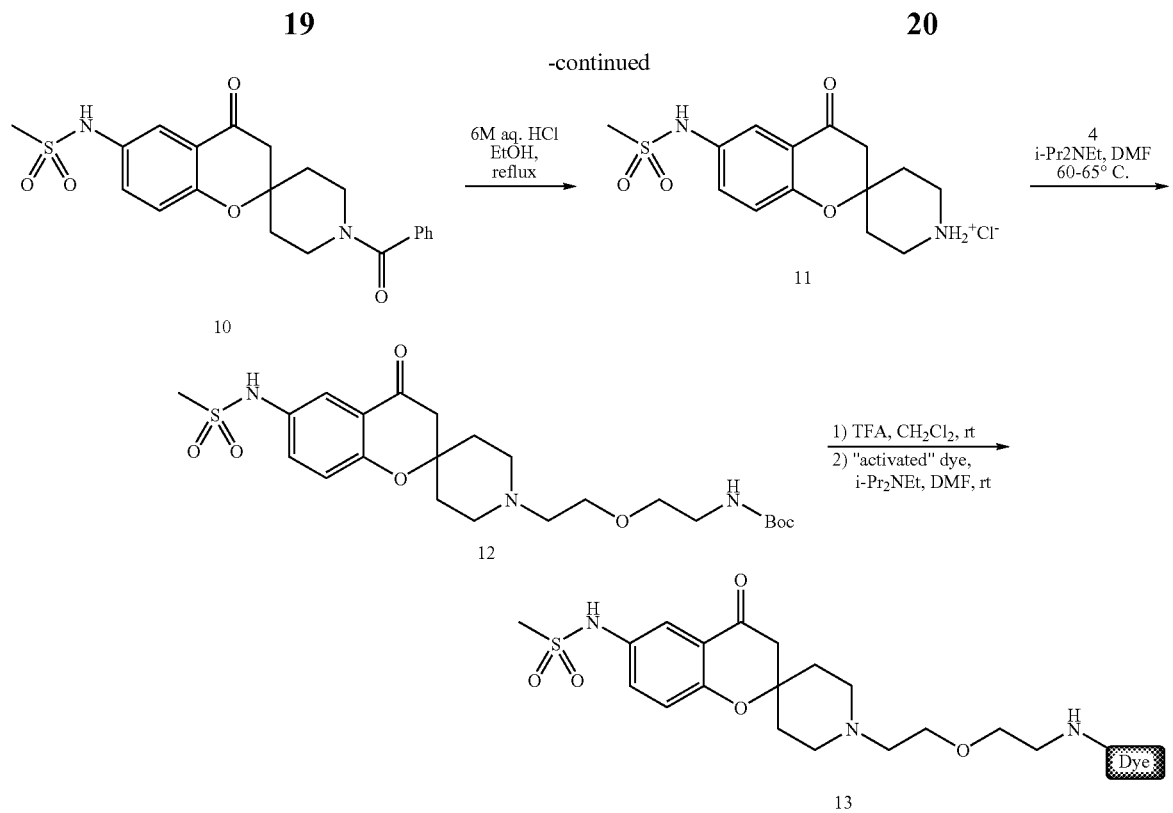

1'-Benzoylspiro[chroman-2,4'-piperidin]-4-one (7)

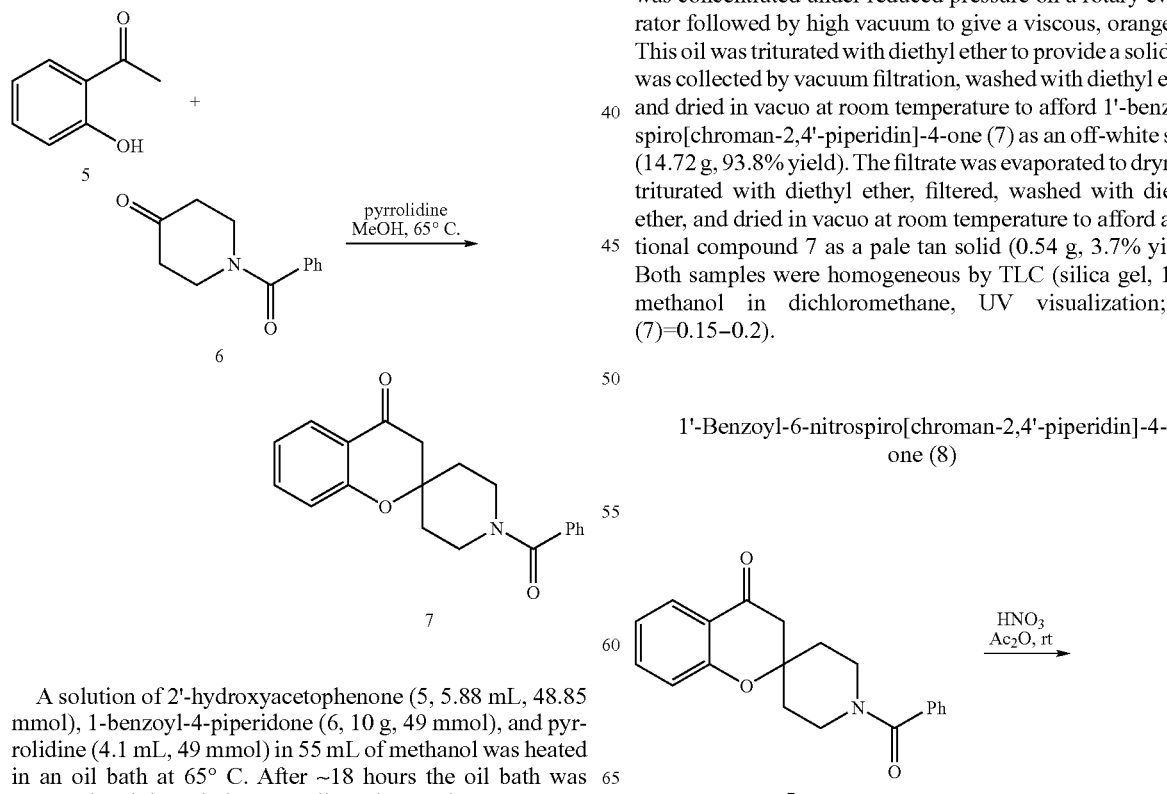

A solution of 2'-hydroxyacetophenone (5, 5.88 mL, 48.85 mmol), 1-benzoyl-4-piperidone (6, 10 g, 49 mmol), and pyrrolidine (4.1 mL, 49 mmol) in 55 mL of methanol was heated in an oil bath at 65° C. After ~18 hours the oil bath was removed and the solution was allowed to cool to room temperature. Additional 1-benzoyl-4-piperidone (6, 100 mg, 0.5 mmol) was added and heating at 65° C. was resumed. After an additional ~2.5 hours the oil bath was removed and the solution was allowed to cool to room temperature. This mixture was concentrated under reduced pressure on a rotary evaporator followed by high vacuum to give a viscous, orange oil. This oil was triturated with diethyl ether to provide a solid that was collected by vacuum filtration, washed with diethyl ether, and dried in vacuo at room temperature to afford 1'-benzoylspiro[chroman-2,4'-piperidin]-4-one (7) as an off-white solid (14.72 g, 93.8% yield). The filtrate was evaporated to dryness, triturated with diethyl ether, filtered, washed with diethyl ether, and dried in vacuo at room temperature to afford additional compound 7 as a pale tan solid (0.54 g, 3.7% yield). Both samples were homogeneous by TLC (silica gel, 1.5% methanol in dichloromethane, UV visualization; $R_f$ (7)=0.15–0.2).

1'-Benzoyl-6-nitrospiro[chroman-2,4'-piperidin]-4-one (8)

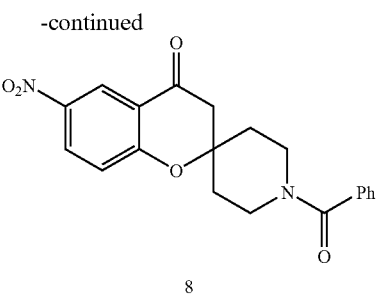

8

1'-Benzoylspiro[chroman-2,4'-piperidin]-4-one (7, 12.6 g, 39.2 mmol) was suspended in 120 mL of acetic anhydride under argon with vigorous stirring. The mixture was cooled to 0-5° C. in an ice bath and fuming nitric acid (15 mL) was added dropwise. The suspended solid dissolved as the nitric acid was added. After the addition was completed, the reaction was stirred at ice bath temperature for 5 minutes and then allowed to warm to room temperature. After ~45 minutes at room temperature, the reaction rapidly became exothermic and was cooled again in an ice bath. After ~1 hour total reaction time, TLC (silica gel, 50:50 ethyl acetate-hexanes, iodine and UV visualization) of a small aliquot (quenched into saturated aqueous sodium carbonate and extracted into ethyl acetate) showed multiple products but complete consumption of starting compound 7 [$R_f$(7)=0.3–0.4]. After ~1.5 hours total reaction time the reaction mixture was poured into 300 mL of ice-cold saturated aqueous sodium carbonate. After the mixture stirred for a few minutes, solid sodium carbonate was added until the solution reached pH 6-7. This solution was extracted with three 200 mL portions of ethyl acetate. The organic extracts were combined, dried over anhydrous sodium sulfate, filtered, and concentrated under reduced pressure on a rotary evaporator to afford an orange-brown foam (16.6 g).

This material was combined with 0.62 g of material from a previous, smaller-scale reaction, and preabsorbed onto silica gel by dissolving in ethyl acetate, adding Silica Gel 60 (70-230 mesh, 50 g), and removing solvent by rotary evaporation under reduced pressure. The resulting powder was applied to the top of a slurry-packed (with 10:90 ethyl acetate-hexanes) 100 g Silica Gel 60 (70-230 mesh) flash chromatography column and eluted successively with 10:90 ethyl acetate-hexanes, 20:80 ethyl acetate-hexanes, 30:70 ethyl acetate-hexanes, 40:60 ethyl acetate-hexanes, and 50:50 ethyl acetate-hexanes, collecting ~125 mL fractions. Based on TLC (silica gel, 50:50 ethyl acetate-hexanes), fractions were combined and concentrated under reduced pressure on a rotary evaporator to provide 8.33 g of slightly impure (by TLC as above) yellow solid.

This material was again preabsorbed onto silica gel by dissolving in dichloromethane, adding Silica Gel 60 (70-230 mesh, 25 g), and removing solvent by rotary evaporation under reduced pressure. The resulting powder was applied to the top of a slurry-packed (with 50:50 ethyl acetate-hexanes) 335 g Silica Gel 60 (70-230 mesh) flash chromatography column and eluted successively with 50:50 ethyl acetate-hexanes and 60:40 ethyl acetate-hexanes, collecting ~125 mL fractions. Based on TLC (silica gel, 1:1 ethyl acetate-hexanes), fractions were combined and concentrated under reduced pressure on a rotary evaporator to provide 6.59 g of yellow foamy solid that was still slightly impure by TLC (silica gel, 50:50 ethyl acetate-hexanes or 3% methanol in dichloromethane, UV visualization).

This material was repurified by flash chromatography on 264 g of Silica Gel 60 (70-230 mesh), eluting successively with dichloromethane, 1% methanol in dichloromethane, and 2% methanol in dichloromethane, collecting ~125 mL fractions. Based on TLC (silica gel, 3% methanol in dichloromethane, UV visualization), fractions were combined and concentrated under reduced pressure on a rotary evaporator to afford 1'-benzoyl-6-nitrospiro[chroman-2,4'-piperidin]-4-one (8, 6.5 g, 45% yield) as a pale yellow foamy solid. By TLC (silica gel, 3% methanol in dichloromethane, UV visualization), this material contained one major component ($R_f$=0.2–0.3) plus a minor contaminant ($R_f$=0.14–0.17).

6-Amino-1'-benzoylspiro[chroman-2,4'-piperidin]-4-one (9)

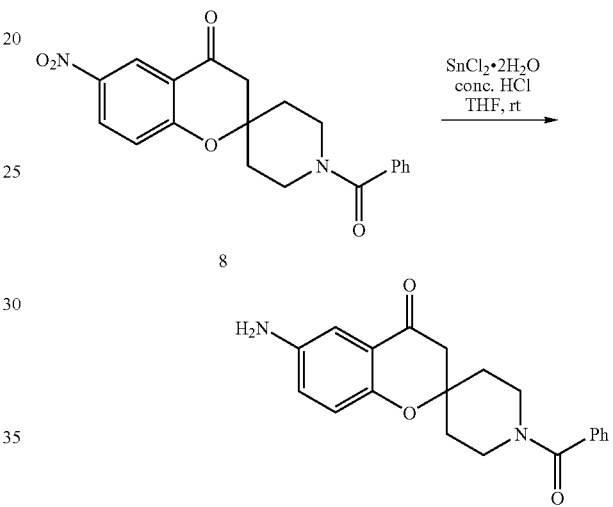

A solution of tin(II) chloride dihydrate (25.4 g, 112 mmol) in 152 mL of concentrated hydrochloric acid was added dropwise, over ~50 minutes, to a solution of 1'-benzoyl-6-nitrospiro[chroman-2,4'-piperidin]-4-one (8, 5.9 g, 16 mmol) in 152 mL of tetrahydrofuran under an argon atmosphere. The reaction mixture was then stirred at room temperature. After ~2 hours total, TLC (silica gel, 10% methanol in dichloromethane, UV visualization, $R_f$ (8)=0.75–0.85) of a small aliquot (quenched into excess aqueous sodium hydroxide and extracted into ethyl acetate) showed that the reaction was complete. The reaction mixture was cooled to 0-5° C. in an ice bath, and 40% aqueous sodium hydroxide was added dropwise until the solution reached pH 11-13. The resulting solution was extracted with three 150 mL portions of ethyl acetate, and the combined ethyl acetate extracts were washed successively with 50 mL portions of water and saturated aqueous sodium chloride. The organic extract was dried over anhydrous sodium sulfate, filtered, and concentrated under reduced pressure on a rotary evaporator followed by high vacuum to give 8.2 g of viscous, yellow oil that showed several spots (one major) on TLC [silica gel, 10% methanol in dichloromethane ($R_f$ 0.4-0.65) or 3% methanol in dichloromethane ($R_f$ 0.2–0.35), UV visualization].

This material was purified by flash chromatography on 220 g of Silica Gel 60 (230-400 mesh) eluting successively with dichloromethane and 2% methanol in dichloromethane, collecting ~200 mL fractions. Based on TLC (silica gel, 10% methanol in dichloromethane, UV visualization), fractions were combined and concentrated under reduced pressure on a rotary evaporator followed by high vacuum to provide 4.2 g of orange residue that showed several spots by TLC.

This material was repurified by flash chromatography on 200 g of Silica Gel 60 (230-400 mesh) eluting successively with 40:60 ethyl acetate-toluene, 50:50 ethyl acetate-toluene, and 70:30 ethyl acetate-toluene, collecting ~125 mL fractions. Based on TLC (silica gel, 1:1 ethyl acetate-toluene, UV visualization), fractions were combined and concentrated under reduced pressure on a rotary evaporator followed by high vacuum to provide 2.15 g (39% yield) of 6-amino-1'-benzoylspiro-[chroman-2,4'-piperidin]-4-one (9) as a yellow solid that was nearly homogeneous by TLC [$R_f$(9)=0.25-0.3, silica gel, 1:1 ethyl acetate-toluene, UV visualization].

N-(1-Benzoyl-4-oxospiro[chroman-2,4'-piperidine]-6-yl)methanesulfonamide (10)

cool to room temperature (some precipitation) and then cooled in the refrigerator at 0-5° C. The solid that precipitated was collected by vacuum filtration, washed with ice-cold 1:1 methanol-ethanol, and dried in vacuo at ambient temperature to afford 0.86 g (38% yield) of N-(1'-benzoyl-4-oxospiro[chroman-2,4'-piperidine]-6-yl)methanesulfonamide (10) as a light pink solid. This material was homogeneous by TLC (silica gel, 5% methanol in dichloromethane, UV visualization, $R_f$(10)=0.3-0.35).

An additional 0.42 g (18% yield) of N-(1-benzoyl-4-oxospiro[chroman-2,4'-piperidine]-6-yl)-methanesulfonamide (10) as a light pink solid was obtained by evaporating the mother liquor to dryness under reduced pressure by rotary evaporation followed by recrystallization of the residue from 2:1 methanol-ethanol. This material was homogeneous by TLC (silica gel, 5% methanol in dichloromethane, UV visualization, $R_f$(10)=0.3-0.35).

N-(4-Oxospiro[chroman-2,4'-piperidine]-6-yl)methanesulfonamide hydrochloride (11)

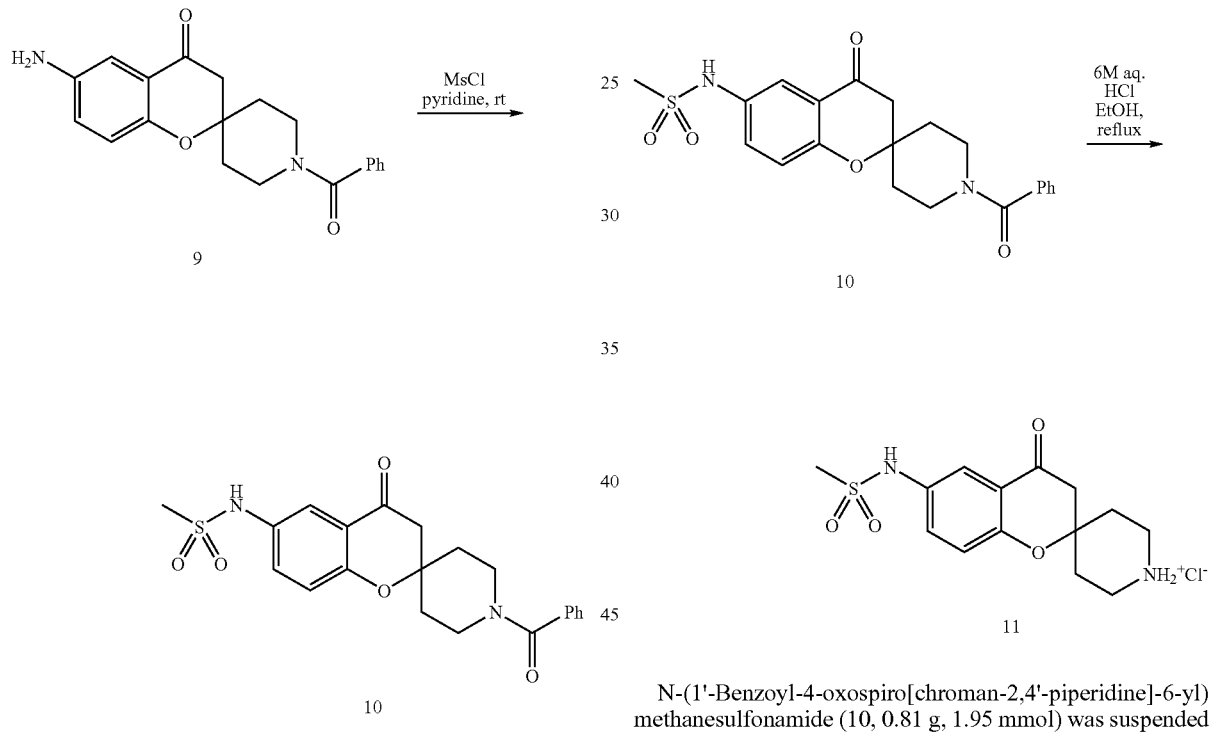

Methanesulfonyl chloride (0.51 mL, 6.6 mmol) was added to a solution of 6-amino-1'-benzoylspiro-[chroman-2,4'-piperidin]-4-one (9, 1.85 g, 5.50 mmol) in 18.5 mL of pyridine. The reaction mixture was stirred at room temperature. After ~1.5 hours, TLC (silica gel, 1:1 ethyl acetate-toluene, UV visualization) of a small aliquot (quenched into ice-cold 3 M aqueous hydrochloric acid and extracted into ethyl acetate) showed that the reaction was complete [$R_f$(9)=0.25-0.3, $R_f$(10)=0.15-0.25]. After ~2 hours total the reaction mixture was poured into 75 mL of ice cold 3 M aqueous hydrochloric acid and stirred for ten minutes. The solid was collected by vacuum filtration, washed with water, and dried in vacuo at ambient temperature to give 2.17 g of pink solid. This material was suspended in a mixture of methanol (50 mL) and ethanol (50 mL) and heated to boiling. Additional methanol was added until dissolution was complete and the hot solution was filtered (gravity). The resulting solution was allowed to N-(1'-Benzoyl-4-oxospiro[chroman-2,4'-piperidine]-6-yl)methanesulfonamide (10, 0.81 g, 1.95 mmol) was suspended in a mixture of absolute ethanol (10 mL) and 6 M aqueous hydrochloric acid (10 mL) and stirred at 85-90° C. in an oil bath. After 1 hour the oil bath temperature was increased to 95° C. After ~3.5 hours at 95° C. the reaction was allowed to cool to room temperature. TLC (silica gel, 10% methanol in dichloromethane, UV visualization) showed no remaining starting material [$R_f$(10)=0.65-0.7]. Solvent was removed under reduced pressure on a rotary evaporator. Ethanol was added to the residue and then evaporated to dryness under reduced pressure on a rotary evaporator. The ethanol addition and evaporation to dryness was repeated two more times. The residue was dried in vacuo to afford 0.77 g (114% yield) of N-(4-oxospiro[chroman-2,4'-piperidine]-6-yl)methanesulfonamide hydrochloride (11) as a light yellow solid that was homogeneous by TLC [silica gel, 10% methanol in dichloromethane containing a small amount of concentrated aqueous ammonium hydroxide, UV visualization, $R_f$(11)= 0.12-0.19]. Mass spec: m/z=311.2 [M+H]$^+$ tert-Butyl 2-(2-(6-(methylsulfonamido)-4-oxospiro[chroman-2,4'-piperidine]-1'-yl)ethoxy)ethylcarbamate (12)

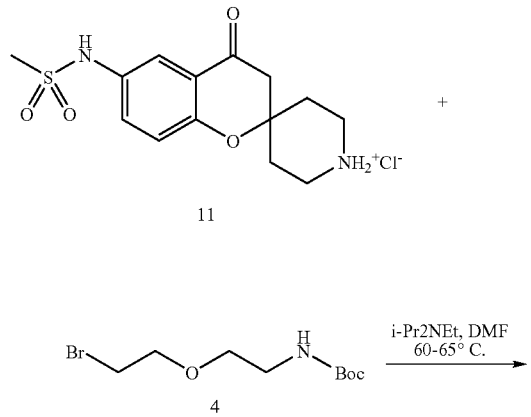

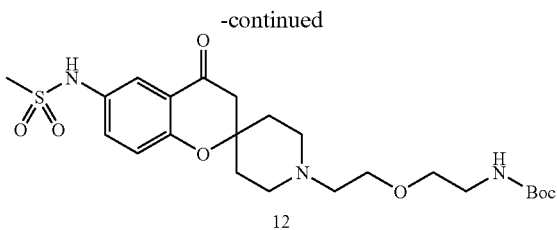

A solution of N,N-diisopropylethylamine (1.3 mL, 7.5 mmol), tert-butyl 2-(2-bromoethoxy)ethyl-carbamate (4, 0.59 g, 2.2 mmol), and N-(4-oxospiro[chroman-2,4'-piperidine]-6-yl)methanesulfon-amide hydrochloride (11, 0.5 g, 1.4 mmol) in 10 mL of anhydrous DMF was stirred at 60-65° C. After ~24 hours TLC (silica gel, 10% methanol in dichloromethane, UV visualization) showed almost complete disappearance of starting amine 11 ($R_f$=0.02–0.06) and appearance of one major new product ($R_f$=0.35-0.45). The reaction was allowed to cool to room temperature and 10 mL of water was added. The resulting mixture was transferred to a separatory funnel with the aid of ethyl acetate and the layers were separated. The aqueous layer was extracted with 20 mL of ethyl acetate. The organic extracts were combined, washed successively with 10 mL portions of water and saturated aqueous sodium chloride, dried over anhydrous sodium sulfate, filtered, and concentrated under reduced pressure on a rotary evaporator followed by high vacuum to provide 0.94 g of orange-brown oil.

This material was combined with 94 mg from a previous, smaller reaction and purified by flash chromatography on 43 g of Silica Gel 60 (230-400 mesh), eluting with 5% methanol in dichloromethane and collecting ~40 mL fractions. Based on TLC (silica gel, 10% methanol in dichloromethane, UV visualization) fractions were combined and concentrated under reduced pressure on a rotary evaporator to afford 0.51 g (59% combined yield) of tert-butyl 2-(2-(6-(methylsulfonamido)-4-oxospiro[chroman-2,4'-piperidine]-1'-yl)ethoxy) ethylcarbamate (12) as a yellow foam that was homogeneous by TLC($R_f$=0.4–0.5). Mass spec: m/z=498.18 $[MH]^+$ $^1$H NMR (300 MHz, CDCl$_3$): δ 1.4 (s, 9H), δ 1.9-2.6 (m, 8H), δ 2.65 (s, 2H), δ 2.9 (s, 3H), δ 3.1-3.6 (m, 8H), δ 5.1 (br s, 1H), δ 6.9-7.6 (m, 4H).

Fluorescent Tracer (13)

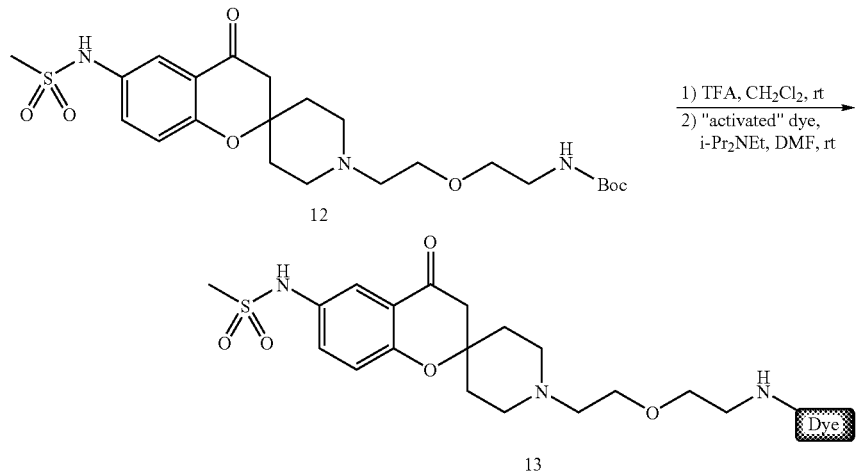

A solution of tert-butyl 2-(2-(6-(methylsulfonamido)-4-oxospiro[chroman-2,4'-piperidine]-1'-yl)ethoxy)ethylcarbamate (12, 5.0 mg, 0.010 mmol) in a mixture of dichloromethane (0.9 mL) and trifluoroacetic acid (TFA, 0.1 mL) was stirred at room temperature for ~3 hours. This solution was evaporated to dryness under reduced pressure on a rotary evaporator at <35° C. Toluene (~1 mL) was added and the solution was evaporated to dryness under reduced pressure on a rotary evaporator at <35° C. The toluene addition/evaporation sequence was repeated one or two more times.

The residue was dissolved in 4.0 mL of anhydrous DMF and 1.0 mL aliquots of the solution were transferred to 5 mL round bottom flasks containing ~1 mg of "amine-reactive" [isothiocyanate, carboxylic acid succinimidyl ester, or carboxylic acid STP (4-sulfo-2,3,5,6-tetrafluorophenyl) ester] fluorescent dye. Anhydrous diisopropylethylamine (0.2 mL) was added to each flask. The flasks were wrapped with aluminum foil to block the light and the reactions were stirred at room temperature, under argon, overnight (16-20 hours). Methanol (0.5 mL) was added to each flask and the solution was stirred at room temperature for 1-3 hours. Solvent was removed under reduced pressure on a rotary evaporator at <35° C. Toluene (~1 mL) was added and the solution was evaporated to dryness under reduced pressure on a rotary evaporator at <35° C. The toluene addition/evaporation sequence was repeated one or two more times. The resulting material was purified by preparative HPLC. (The same general procedure was employed to prepare additional fluorescent tracers of general formula 13, from intermediate compound 14; fluorescent tracers of general formula 20, from intermediate compound 17; and fluorescent tracers of general formula 21, from intermediate 19, all of which tracers are listed in Table 1).

Representative HPLC purification conditions:
Column: Zorbax RX, C-8, 5 microns, 4.6 mm×25 cm
Buffer A: 0.1% TFA, 10% acetonitrile
Buffer B: 0.085% TFA, 90% acetonitrile
Gradient: 2-25 min 10-50% B; 35-45 min 50-100% B
Flow rate: 1.0 mL/min
Injection: 100 µL of 1.4 mM in Buffer A

N-(1'-(2-(2-Aminoethoxy)ethyl)-4-oxospiro[chroman-2,4'-piperidine]-6-yl)methanesulfon-amide dihydrochloride (14)

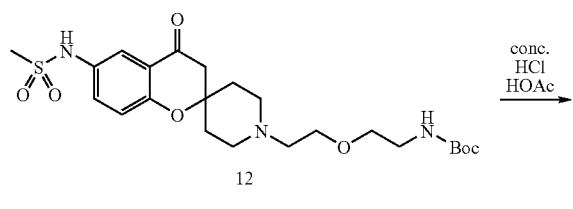

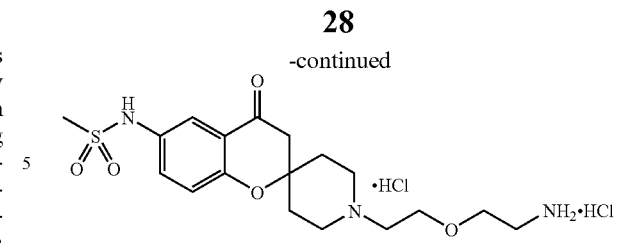

Ten drops of concentrated hydrochloric acid was added to a solution of tert-butyl 2-(2-(6-(methylsulfonamido)-4-oxospiro[chroman-2,4'-piperidine]-1'-yl)ethoxy)ethylcarbamate (12, 0.51 g, 1.02 mmol) in 5 mL of glacial acetic acid and the resulting solution was stirred at room temperature. After ~1.5 hours, TLC (silica gel, 10% methanol in dichloromethane, UV visualization) shows complete disappearance of starting compound 12 ($R_f$=0.2–0.3) and a new spot at the origin. Volatile components were removed under reduced pressure on the rotary evaporator. Toluene (~10 mL) was added and evaporated under reduced pressure on the rotary evaporator. The toluene addition and evaporation was repeated two more times and the residue was dried under high vacuum. The resulting residue was triturated with 3 mL of diethyl ether, resulting in formation of a tan solid. The diethyl ether was removed under reduced pressure on the rotary evaporator followed by high vacuum to give a tan solid.

(R)-tert-Butyl 2-(2-(4-hydroxy-6-(methylsulfonamido)spiro[chroman-2,4'-piperidine]-1'-yl)ethoxy) ethylcarbamate (16)

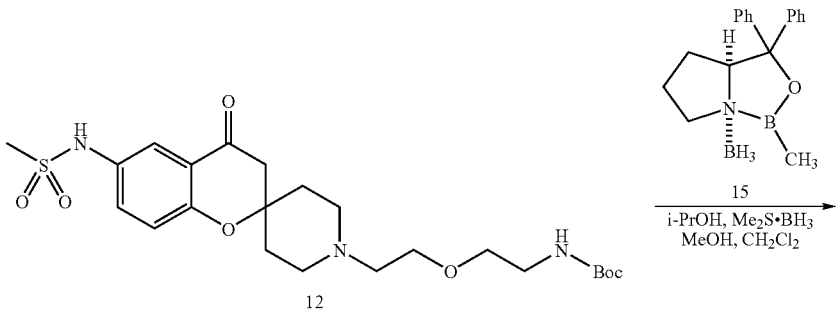

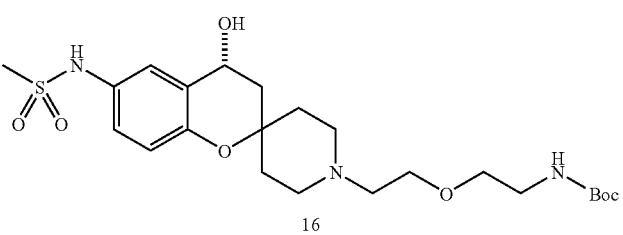

tert-Butyl 2-(2-(6-(methylsulfonamido)-4-oxospiro[chroman-2,4'-piperidine]-1'-yl)ethoxy)ethyl-carbamate (12, 0.25 g, 0.50 mmol) was dissolved in 5 mL of dichloromethane containing 0.038 mL (0.5 mmol) of 2-propanol and the solution was cooled to −20° C. Borane dimethyl sulfide complex (Me$_2$S.BH$_3$, 0.126 mL, ~1.26 mmol) was added dropwise and the solution was stirred at −20° C. for 1 hour. (S)-Tetrahydro-1-methyl-3,3-diphenyl-1H,3H-pyrrolo-[1,2-c][1,3,2]oxazaborole-borane complex (15, 15 mg, 0.05 mmol; prepared from (S)-tetrahydro-1-methyl-3,3-diphenyl-1H,3H-pyrrolo[1,2-c][1,3,2]oxazaborole as described in Xavier, L. C.; et al. Org. Syn. 1998, Coll. Vol. 9, 676) was added in a single portion and the mixture was stirred at −20° C. for 30 minutes. The reaction mixture was allowed to warm slowly (over ~30 minutes) to 0° C. and then stirred at 0° C. for 2.5-3 hours. TLC (silica gel, 10% methanol in dichloromethane, UV visualization) show complete disappearance of starting ketone 12 (R$_f$=0.4-0.5). Methanol (4.5 mL) was added and the reaction was allowed to warm to room temperature. The reaction flask was fitted with a short path distillation head, placed in an oil bath, and heated to remove volatile components until the distillate temperature reached 62° C. An additional 5 mL of methanol was added and the flask was heated in an oil bath at ~75° C. for 30 minutes as about half of the methanol was removed by distillation. The flask was cooled to room temperature, acetonitrile (5 mL) was added, and the mixture was evaporated to dryness under reduced pressure on the rotary evaporator followed by high vacuum at ambient temperature, affording a yellow solid (crude 16) that showed multiple components by TLC [silica gel, 10% methanol in dichloromethane or 10% methanol in dichloromethane containing a small amount of aqueous ammonium hydroxide, iodine visualization; R$_f$ (12)=0.35-0.4, R$_f$ (major component)=0.03-0.17 in 10% MeOH/CH$_2$Cl$_2$; R$_f$ (12)=0.47-0.53, R$_f$ (major component)=0.25-0.35 in 10% MeOH/CH$_2$Cl$_2$ containing NH$_4$OH].

This material (crude 16) was purified by flash chromatography on a 10 g Silica Gel 60 (230-400 mesh) column, eluting with 7% methanol in dichloromethane containing 0.2% aqueous ammonium hydroxide and collecting ~10 mL fractions. Based on TLC (silica gel, 10% methanol in dichloromethane, iodine visualization), fractions were combined and concentrated under reduced pressure on a rotary evaporator to afford 195 mg (77% yield) of (R)-tert-butyl 2-(2-(4-hydroxy-6-(methylsulfonamido)spiro[chroman-2,4'-piperidine]-1'-yl)ethoxy)ethylcarbamate (16) as a foamy, white solid. $^1$H NMR: consistent with the desired product (16). Mass spec: m/z=500.1551 (expected for [M+H]$^+$=500.2425)

N-(1'-(2-(2-aminoethoxy)ethyl)spiro[chromene-2,4'-piperidine]-6-yl)methanesulfonamide dihydrochloride (17)

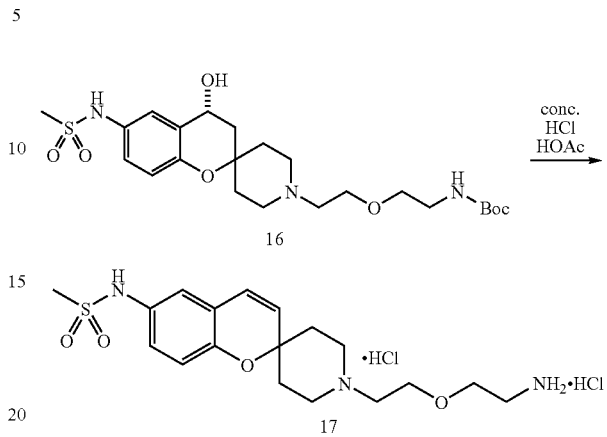

(R)-tert-butyl 2-(2-(4-hydroxy-6-(methylsulfonamido)spiro[chroman-2,4'-piperidine]-1'-yl)ethoxy)-ethylcarbamate (16, 193 mg, 0.386 mmol) was dissolved in 5 mL of glacial acetic acid. The solution was cooled in a cool water bath and 8 drops of concentrated hydrochloric acid were added. The water bath was removed and the reaction was allowed to warm to room temperature. After 3 hours, TLC (silica gel, 10% methanol in dichloromethane containing a small amount of aqueous ammonium hydroxide, iodine visualization) showed complete disappearance of starting compound 16 (R$_f$=0.3-0.35) and appearance of a single new compound (17, R$_f$=0.18-0.25). The reaction mixture was concentrated to dryness under reduced pressure on a rotary evaporator. Toluene was added and evaporated to dryness under reduced pressure on a rotary evaporator. This toluene addition and evaporation was repeated two more times and the residue was dried under high vacuum at ambient temperature, giving a viscous yellow residue. This material was triturated with diethyl ether to give 210 mg (120% yield) of N-(1'-(2-(2-aminoethoxy)ethyl)spiro[chromene-2,4'-piperidine]-6-yl)methanesulfonamide dihydrochloride (17) as a pale yellow solid. Mass spec: m/z=382.13 [M+H]$^+$ tert-Butyl 2-(2-(4-(hydroxyimino)-6-(methylsulfonamido)spiro[chroman-2,4'-piperidine]-1'-yl)ethoxy)ethylcarbamate (18)

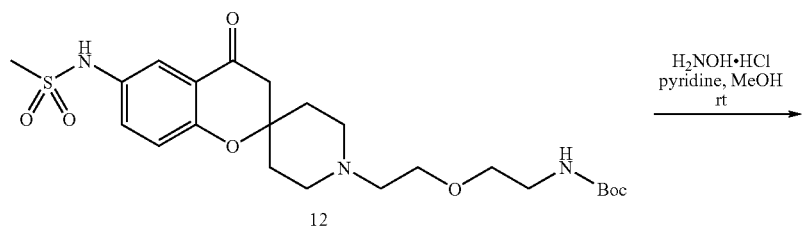

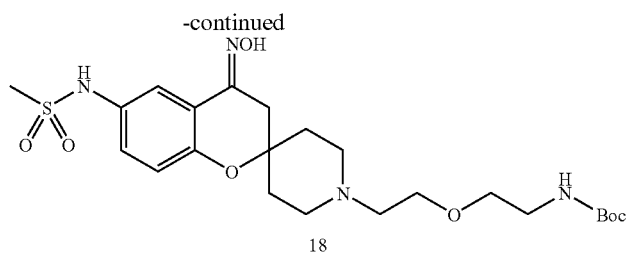

18

Anhydrous pyridine (40 μL, 0.5 mmol) and hydroxylamine hydrochloride (8 mg, 0.11 mmol) were added to a solution of tert-butyl 2-(2-(6-(methylsulfonamido)-4-oxospiro[chroman-2,4'-piperidine]-1'-yl)ethoxy)ethylcarbamate (12, 50 mg, 0.10 mmol) in 5 mL of anhydrous methanol. This solution was stirred at room temperature for ~1 hour and then at ~60° C. for ~1 hour. Additional hydroxylamine hydrochloride (6.2 mg, 0.09 mmol) and anhydrous pyridine (40 μL, 0.5 mmol) were added and stirring was continued at 60-65° C. for ~1 hour. More hydroxylamine hydrochloride (13.9 mg, 0.20 mmol) was added and stirring was continued at 60-65° C. for ~80 minutes. Hydroxylamine hydrochloride (7 mg, 0.10 mmol) was added and stirring was continued at 60-65° C. for ~2 hours. TLC (silica gel, 10% methanol in dichloromethane, UV visualization) showed complete disappearance of starting ketone 12 ($R_f$=0.35-0.4) and a single new spot (18, $R_f$=0.18-0.27). The reaction mixture was concentrated to dryness under reduced pressure on a rotary evaporator. The residue was dissolved in 5 mL of ethyl acetate and extracted successively with 10 mL of 0.5 M aqueous hydrochloric acid, mL of water, and 5 mL of saturated aqueous sodium chloride. TLC (as above) showed the product (18) in the combined aqueous extracts, which were adjusted to pH ~13 by addition of sodium hydroxide pellets and then to pH ~4 by addition of 3 M aqueous hydrochloric acid. The aqueous solution was extracted with three 20 mL portions of ethyl acetate. The combined ethyl acetate extract was dried over anhydrous sodium sulfate, filtered, and evaporated to dryness under reduced pressure on a rotary evaporator followed by high vacuum overnight to afford 50.3 mg (98% yield) tert-butyl 2-(2-(4-(hydroxyimino)-6-(methylsulfonamido)-spiro[chroman-2,4'-piperidine]-1'-yl)ethoxy)ethylcarbamate (18).

N-(1'-(2-(2-Aminoethoxy)ethyl)-4-(hydroxyimino)spiro[chroman-2,4'-piperidine]-6-yl)methanesulfonamide dihydrochloride (19)

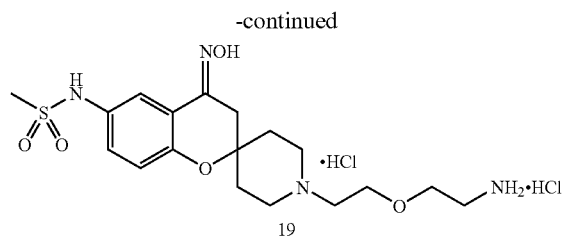

19 tert-Butyl 2-(2-(4-(hydroxyimino)-6-(methylsulfonamido)-spiro[chroman-2,4'-piperidine]-1'-yl)ethoxy)ethylcarbamate (18, 50.3 mg, 0.10 mmol) was dissolved in 1 mL of glacial acetic acid. The solution was cooled in a cool water bath and 2 drops of concentrated hydrochloric acid was added. The water bath was removed and the solution was allowed to warm to room temperature. After 45 minutes, TLC (silica gel, 10% methanol in dichloromethane, UV visualization) showed complete disappearance of starting compound ($R_f$(18)=0.15-0.25) and appearance of a single new product with $R_f$=0. Toluene (5 mL) was added and then evaporated under reduced pressure on a rotary evaporator. This toluene addition and evaporation was repeated two more times and the residue was dried under high vacuum for ~1 hour to afford 39.2 mg (82% yield) of N-(1'-(2-(2-amino-ethoxy)ethyl)-4-(hydroxyimino)spiro[chroman-2,4'-piperidine]-6-yl)methanesulfonamide dihydrochloride (19).

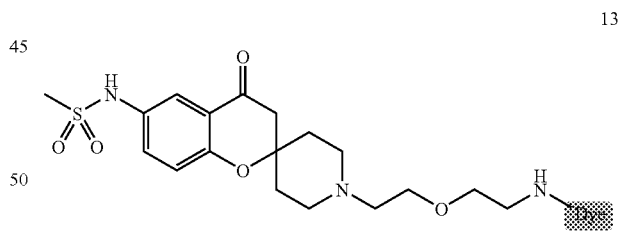

13

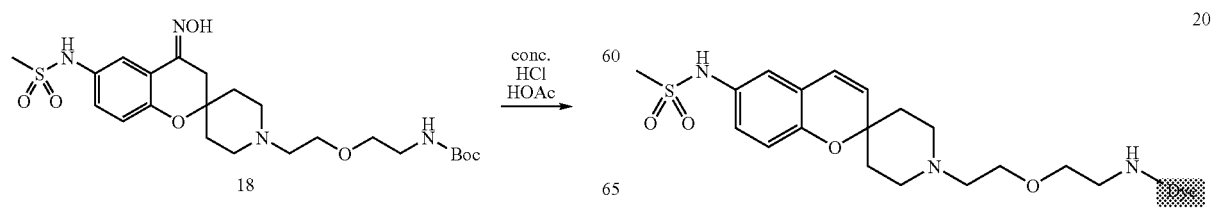

21

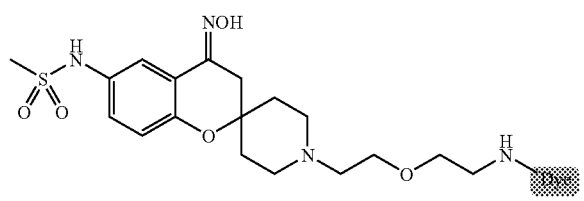

TABLE 1

Fluorescent Tracers of General Formulae 13, 20, and 21

| Compound | Scaffold | Fluorescent Dye | HPLC Retention Time | Purity | Mass Spec Exact Mass | Observed m/z |
|---|---|---|---|---|---|---|
| 20a | Alkene | 5-FAM | 16.3 min | 100% | 739.22 | 739.22 |
| 20b | Alkene | FITC | 19.2 min | 100% | 786.24 | 771.19 |
| 20c | Alkene | Rhodamine Red-X | 25.2 min | ND | 1034.40 | 1034.34 |
| 20d | Alkene | Texas Red-X | 31.2 min | ND | 1082.40 | 1082.34 |
| 20e | Alkene | BODIPY ® TR | 30.6 min | ND | 787.25 | 788.23 |
| 20f | Alkene | BODIPY ® FL | 30.8 min | 100% | 655.28 | 656.27 |
| 20g | Alkene | BODIPY ® TR-X | 30.9 min | ND | 900.33 | 901.34 |
| 20h | Alkene | DDAO | 28.6 min | ND | 770.23 | 771.21 |
| 20m | Alkene | Alexa Fluor ® 546 | 21.2-23.4 min | ND | 1322.28 | 1322.27 |
| 13a | Ketone | 5-FAM | 14.4 min | 100% | 755.21 | 756.19 |
| 13b | Ketone | FITC | 17.9 min | 100% | 786.20 | 786.20 |
| 13c | Ketone | Rhodamine Red-X | 28.1 min | 100% | 1050.39 | 1050.38 |
| 13d | Ketone | Texas Red-X | 30.0 min | 100% | 1098.39 | 1098.39 |
| 13e | Ketone | BODIPY ® TR | 20.3 min | 100% | 803.24 | 804.22 |
| 13f | Ketone | BODIPY ® FL | 27.5 mi | 100% | 671.28 | 672.18 |
| 13g | Ketone | BODIPY ® TR-X | 35.0 min | 100% | 916.33 | 917.31 |
| 13h | Ketone | DDAO | 26.8 min | 100% | 786.23 | 787.19 |
| 13i | Ketone | 5-TAMRA | 26.7 min | 95% | 809.31 | 810.0 |
| 13j | Ketone | 6-TAMRA | 24.0 min | 98% | 809.31 | 810.0 |
| 13k | Ketone | BODIPY ® TMR | 35.3 min | 100% | 777.32 | 778.0 |
| 13l | Ketone | BODIPY ® TMR-X | 35.4 min | 100% | 890.84 | 891.2 |
| 21b | Oxime | FITC | 20.0 min | 100% | 801.21 | 802.27 |
| 21e | Oxime | BODIPY ® TR | 16.0 min | 100% | 818.25 | 819.33 |
| 21g | Oxime | BODIPY ® TR-X | 19.6 min | 100% | 931.34 | 932.35 |

Materials and Methods

Membrane Preparations

The hERG-T-REx™ 293 cell line (Invitrogen, Carlsbad, Calif.) was used to generate membrane preparations for testing the affinity of fluorescent tracer molecules. Cells were maintained following the manufacturers recommended protocol at 37° C. in 5% $CO_2$ atmosphere, and were induced to express the hERG channel by the addition of 1 μg/mL doxycycline (MP biomedicals, Solon, Ohio). Following a 24 hr of induction, cells were washed with divalent ion free PBS (Invitrogen), harvested and washed once with Versene (Invitrogen) and then spun down at ~500 g for 5 minutes. The cell pellet was kept on ice and resuspended with ice-cold homogenization buffer containing 20 mM HEPES (pH 7.4), 5 mM KCl, 1 mM EDTA, 1 mM PMSF, 0.01 mM E-64, and 10 μg/ml leupeptin. The cells were then homogenized with a Bio Polytron hand held homogenizer (Brinkmann, Westbury, N.Y.), spun down at 40,000 g for 10 min at 4° C., and the supernatant was discarded. The membrane pellet was resuspended in ice-cold homogenization buffer, then homogenized and centrifuged again. The supernatant was discarded and the membrane pellet was resuspended in storage buffer containing 20 mM HEPES (pH 7.4), 5 mM KCl, 1 mM $MgCl_2$, and 1 mM EGTA. The membrane pellet was broken up by pipetting, and sonicated until a uniform suspension was achieved. The resulting membrane preparation was aliquotted and stored at −80° C. During the process of assay optimization, the homogenization and storage buffers were replaced with the experimentally-determined assay buffer containing 25 mM HEPES (pH 7.5), 15 mM KCl, 1 mM $MgCl_2$, and 0.05% Pluronic F-127.

Radioligand Binding Assays

For saturation binding assays, hERG membranes were diluted into assay buffer containing 60 mM KCl, 71.5 mM NaCl, 1 mM $CaCl_2$, 2 mM $MgCl_2$, 0.1% BSA, and 10 mM HEPES, pH 7.4. Next, 80 μL of the membrane/buffer mixture was added to each well of a 96-well deep-well assay block (Corning, Lowell., MA) containing either 5 μL of 20× unlabeled astemizole (to determine non-specific binding) or empty wells (total binding). Labeled [$^3$H]-astemizole was added as 20 μL of a 5× stock of the appropriate concentration. Non-specific binding was determined in parallel for each concentration of label assayed. All assays were performed using triplicate wells, and the final concentration of membrane protein in the assay was 20 μg/well.

To determine $IC_{50}$ values of test compounds, hERG membranes were diluted into assay buffer and 80 μL of membrane/buffer mixture was added per well to a 96 well deep well assay block containing either 5 μL of 20× unlabeled astemizole (non-specific binding), 5 μL of 20× reference compounds or empty wells (total binding). [$^3$H]-astemizole was added as 20 μL of a 5× stock. Test compounds were typically tested using eight concentrations in duplicate wells. The final concentration of membrane protein in the assay was 10 μg/well and the final concentration of [$^3$H]-astemizole was 1.5 nM.

After gentle vortexing to mix, the assay blocks were covered with parafilm and incubated at room temperature for two hours. The reaction was terminated by filtration through GF/B Unifilters (PerkinElmer, Waltham, Mass.) that had been presoaked for two hours in a 0.3% polyethylenimine solution (Sigma-Aldrich, St. Louis, Mo.). The filter plates were then washed with 6-8 volumes of cold (4° C.) wash buffer containing 131.5 mM NaCl, 1 mM $CaCl_2$, 2 mM $MgCl_2$, 10 mM HEPES and 0.1% BSA and then dried on a hot block at 85° C. for 1-2 hours. The bottom of the plates were sealed and 50 µL of Microscint 20 (PerkinElmer) was added to each well. The top of the plate was sealed with TopSeal (PerkinElmer) and the plates were analyzed after a minimum of 2 hours on a TopCount scintillation counter (PerkinElmer).

Patch-Clamp Recording

Cells expressing hERG were plated on 55 mm round coverslips and allowed to adhere in an incubator overnight. Coverslips were placed on a microscope stage in a bath chamber and perfused with PBS or equivalent at 1 mL/min. After obtaining a GΩseal, currents were recorded using the whole-cell recording mode (see, Hamill, O. P.; Marty, A.; Neher, E.; Sakmann, B.; Sigworth, F. J., Improved patch-clamp techniques for high-resolution current recording from cells and cell-free membrane patches. *Pflugers Arch* 1981, 391, (2), 85-100). Cells were held at −90 mV, and the currents were filtered at 667 Hz and sampled at 2.0 kHz using an EPC10/2 amplifier (HEKA, Oberkochen, Germany). Voltage-dependent activation curves were obtained by stepping the command potential to −70 mV for 50 ms, then stepping the command potential through the range of −70 to +40 mV in 10 mV increments for a duration of 2 s, returning the command potential to −70 mV for 2 s and then returning to the holding potential of −90 mV, every 5 s.

Cell Engineering

An expression vector was constructed using a CMV promoter to drive transcription of a bicistronic element composed of nucleotide sequences encoding the hERG channel and the CD8 cell surface marker. Translation of the two proteins was linked by an internal ribosomal entry site sequence (IRES). A puromycin-resistance marker was included on the expression vector to provide a means of selecting cells wherein stable, genomic incorporation of the expression cassette had occurred. A culture of 293 cells was maintained in 293 growth medium composed of high glucose D-MEM+Na–pyruvate+GlutaMAX™ supplemented with FBS (10%), MEM-NEAA, HEPES, and P/S at 37° C. in 5% $CO_2$. The day before transfection, the cells were plated at ~80% confluency into 6-well dishes (Corning). Cells were transfected with plasmid DNA using Lipofectamine™ LTX and Plus™ reagents (Invitrogen) according to the manufacturer's protocol. The next day, the cells were harvested, expanded into a T175 flask (Corning), and put under selection by the addition of puromycin (Sigma) to the medium to a final concentration of 0.3 µg/mL. Cells were maintained and split under selection for ~3 weeks to generate a stable pool of hERG-CD8-expressing 293 cells.

Immunocytochemistry and FACS

For single-cell FACS, cells were washed with PBS and harvested with trypsin-EDTA (Invitrogen), which was then inactivated with at least an equal volume of 293 growth medium. Cells were counted, spun down at 1000×g for 5 min and resuspended in PBS supplemented with 0.1% BSA at a density of $10 \times 10^6$ cells/mL. Following the manufacturer's suggested protocol, 10 µL of mouse anti-human CD8 Alexa Fluor 488 monoclonal antibody (Invitrogen) was added per $2 \times 10^6$ cells (in 200 µL) and allowed to incubate for 30-60 min at room temperature. Cells were then repeatedly (3 times) spun down at 1000×g for 5 minutes and washed in PBS+0.1% BSA, before being resuspended in 2 mL PBS+0.1% BSA and filtered to achieve a disperse single cell suspension at ~$1 \times 10^6$ cells/mL for sorting. Cell suspensions were then run on a FACSVantage (BD Biosciences, San Jose, Calif.) using the 488 nm laser line and collecting with an emission filter centered at 530 nm. Single cells from the top 10% of the stained population were isolated into 96-well microplates and were expanded for ~3 weeks.

Immunocytochemistry was performed in 96-well microplates (Corning) by washing cells with PBS and fixing in 4% paraformaldehyde in PBS for 10 min. Cells were permeabilized with 0.25% TritonX-100 in PBS for 3 min, washed three times with PBS and blocked with 1% BSA in PBS for 30 min. Cells were then stained with primary mouse anti-human CD8 monoclonal antibody (2 µg/mL) in PBS for 60 min at room temperature. Primary antibody was washed off three times with 1% BSA in PBS; cells were stained with secondary goat anti-mouse Alexa Fluor 488 (1:500) for 30 min at room temperature, and then washed three times with 1% BSA in PBS and once with PBS. The immunofluorescence was then measured on a Tecan Safire$^2$ plate reader (Tecan Instruments, Raleigh-Durham, N.C.) using 488 nm excitation and 520 nm emission (10 nm bandwidth).

Fluorescence Polarization Assays

Tracer evaluation was conducted by incubating diluted membrane preparations and fluorescent tracer in the presence or absence of 10 µM dofetilide (Sequioa Research Products, Pangboume, UK) in order to assess the degree of hERG-specific (and displaceable) tracer binding. Experiments were performed in a variety of buffers (data not shown), and the optimal FP assay buffer composition was experimentally determined to consist of 25 mM HEPES (pH 7.5), 15 mM KCl, 1 mM $MgCl_2$, and 0.05% Pluronic F-127. Compound-displacement assays were performed by first dispensing 10 µL of assay buffer with or without test compounds to wells of a 384-well untreated polystyrene assay plate (Corning #3677), and then adding 10 µL of a mixture of membrane preparation and tracer at twice the final assay concentration. Reactions were incubated for 2 to 4 hours and then read on a Tecan InfiniTE F500 or Tecan Safire$^2$ microplate reader using polarized excitation and emission filters or monochromator settings that were appropriate to the tracer being evaluated. Optimal conditions for FP assays were determined by titrating a matrix of membrane protein against varying concentrations of fluorescent tracer in the presence and absence of 30 µM E-4031 (Tocris Bioscience, Ellisville, Mo.). These experimentally-determined concentrations of total membrane protein and fluorescent tracer were then used to perform competition assays against a dilution series of compounds known to block the hERG channel. Using the final optimized tracer (Predictor™ hERG Tracer Red), final optimized assay conditions contained 1 nM tracer and 85 µg/mL membrane protein ($B_{max}$ of membrane preparation ~450 pmol/mg) in a 20 µL final assay volume. Assay wells were excited at 530 nm and emission was measured at 585 nm (20 nm bandwidth) using a Tecan Safire2 microplate reader. In experiments designed to measure the amount of non-hERG specific tracer that could be displaced, the assay also contained 30 µM E-4031.

Data Analysis

Data were analyzed using Microsoft® Office Excel 2003 and Prism 4 for Windows (GraphPad Software Inc., San Diego, Calif.).

Identification of a High Affinity Fluorescent Tracer

A series of candidate tracers were synthesized in order to generate compounds which varied in their affinity for the hERG $K^+$ channel. Compound variation was accomplished by combining a number of chemical scaffolds with various functional constituents, linkers and fluorophores (see, Singleton, D. H.; Boyd, H.; Steidl-Nichols, J. V.; Deacon, M.; Groot, M. J.; Price, D.; Nettleton, D. O.; Wallace, N. K.; Troutman, M. D.; Williams, C.; Boyd, J. G., Fluorescently Labeled Analogues of Dofetilide as High-Affinity Fluorescence Polarization Ligands for the Human Ether-a-go-go-Related Gene (hERG) Channel. *J Med Chem* 2007, 50, (13), 2931-2941). Tracer affinity was initially evaluated using a radioligand displacement assay to measure the affinity of the tracer for the hERG K+ channel. A subset of these compounds was determined to bind the hERG K+ channel with high affinity, a finding that suggested one might prove useful as a fluorescent tracer molecule for assay development (FIG. 1).

Generating Membrane Preparations with Higher Specific Activity

The highest-affinity tracers shown in FIG. 1 were examined for their performance in an FP assay using membrane preparations derived from the hERG-T-REX™ 293 cell line. Membrane preparations from this cell line had a specific activity ($B_{max}$ value) of approximately 7 pmol hERG protein/mg of total protein. Initial FP experiments failed to produce a measurable difference in polarization values in the presence or absence of known hERG channel blockers such as E-4031 or dofetilide with any of the candidate tracers, even when using total membrane concentrations as high as 6001 mg/mL in the assay. These results were not surprising given that a robust FP assay requires both a high affinity tracer as well as protein concentrations that are sufficient to ideally bind at least ~50% or more of the tracer in the absence of displacing compounds (see, Huang, X., Fluorescence polarization competition assay: the range of resolvable inhibitor potency is limited by the affinity of the fluorescent ligand. *J Biomol Screen* 2003, 8, (1), 34-8). High specific content of the protein of interest is also desirable in order to minimize non-specific interactions with the membranes or other membrane proteins. Therefore, we sought to increase the $B_{max}$ of the hERG channel membrane preparations by generating a stable pool of 293 cells using a bicistronic vector that coupled expression of the hERG channel to the CD8 receptor by virtue of an IRES element. In such cells, high levels of the CD8 marker would be expected to correlate with high levels of hERG channel. High-expressing cells were isolated by FACS, and cells from the top 10% of the CD8+ population (FIG. 2, panel A) were sorted and isolated as single cells into 96-well plates. Single cell clones were expanded, then stained to identify individual clones with the highest CD8 expression level (FIG. 2, panel B). Of the ~192 clones thus examined, six were isolated for further study and were examined by patch-clamp recording to determine the degree of functional hERG channel expression at the plasma membrane (FIG. 2, panel C). To ensure a true clonal population and to ensure the best cellular substrate for hERG channel containing membranes, one of these clones (clone D) was expanded, and then subjected to a second round of FACS isolation, clonal expansion, and immunocytochemical staining. Membrane protein from the highest-expressing clone was prepared and characterized by radioligand binding, in which a $B_{max}$ of >450 pmol/mg was determined (FIG. 2, panel D). This is a >50-fold increase as compared to the membrane preparations derived from the hERG-T-REx™ 293 cell line.

Fluorescence Polarization Assay Optimization

Using the six candidate high-affinity tracers that were originally identified in the radioligand displacement assay, a membrane preparation from the hERG-CD8 293 cell line was evaluated for use in an FP experiment by titrating a fixed amount of each tracer (1 nM) with increasing concentrations of membrane preparation. The assays were performed in the presence or absence of 10 μM dofetilide in order to discriminate non-specific from specific binding. Of the six candidate tracers, only one (IM-0107) provided an assay window of >100 mP between specific- and non-specific binding at a concentration of membrane required to elicit ~70% bound tracer. Although further assay optimization was possible using this tracer, the excitation and emission spectra of the fluorophore used was similar to that of Texas Red, which falls between those of common "red" (TAMRA-like) or "far-red" (Cy5-like) fluorophores. Because of this, both non-standard filters and a custom dichroic mirror were required in the plate reader (Tecan InfiniTE F-500) for optimal performance. To allow the assay to be easily performed on a variety of commercially-available plate readers, another round of iterative tracer synthesis was undertaken, based on the results of the initial evaluations. In this second round of synthesis, tracer evaluation was facilitated by characterizing tracer performance using the FP assay rather than the more cumbersome radioligand displacement assay.

Figure 3:
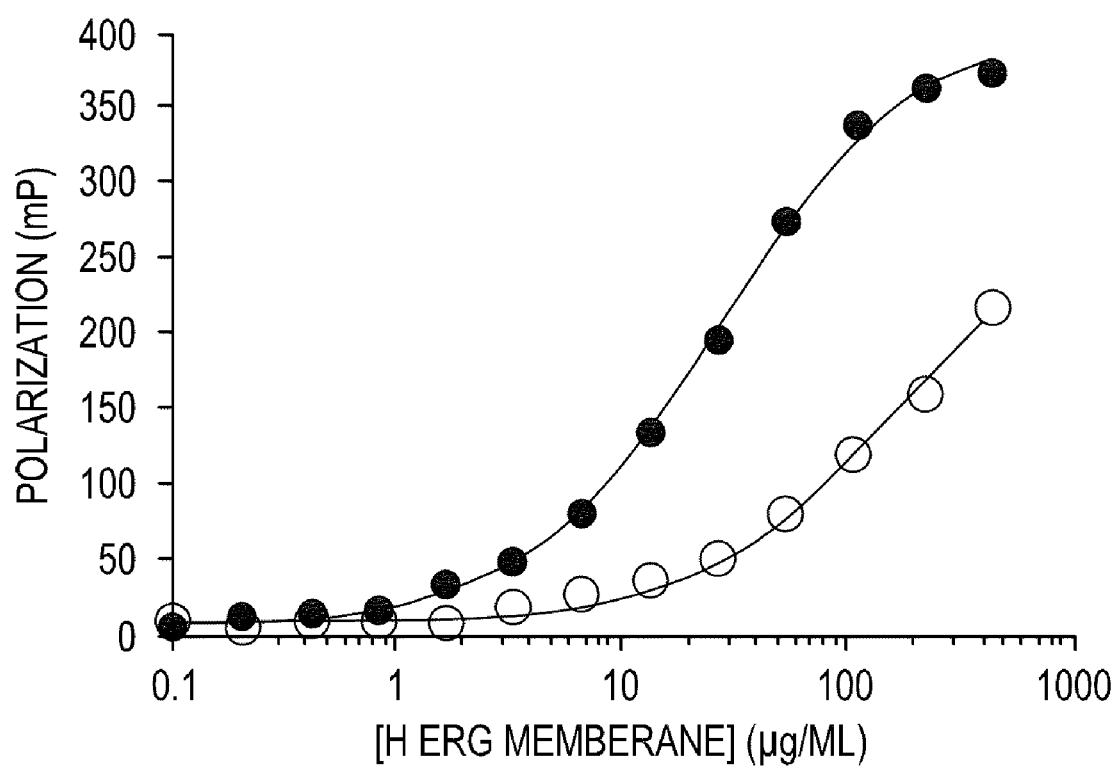
FIG. 3 shows observed polarization values of Predictor™ hERG Tracer Red to hERG-CD8 membranes in the presence (○) or absence (●) of 30 μM E-4031.

This second round of synthesis resulted in the identification of Predictor™ hERG Tracer Red, a tracer with TAMRA-like excitation and emission spectra that showed strong specific binding to hERG-CD8 membranes with a large polarization shift between bound and displaced tracer at a concentration of membrane required for 75% specific binding of tracer (85 μg/mL total protein, FIG. 3). As with all of the tracers evaluated, substantial non-specific binding of the tracer was observed, as seen by the membrane-dependent increase in mP values in the presence of saturating E-4031. This polarization signal was not an artifact due to scattered light from the membranes, as the specific signal from the tracer in the presence of membrane was >40-fold that of membrane alone in both the parallel and perpendicular emission channels for all measurements when using the Safire$^2$ plate reader.

Figure 4A:
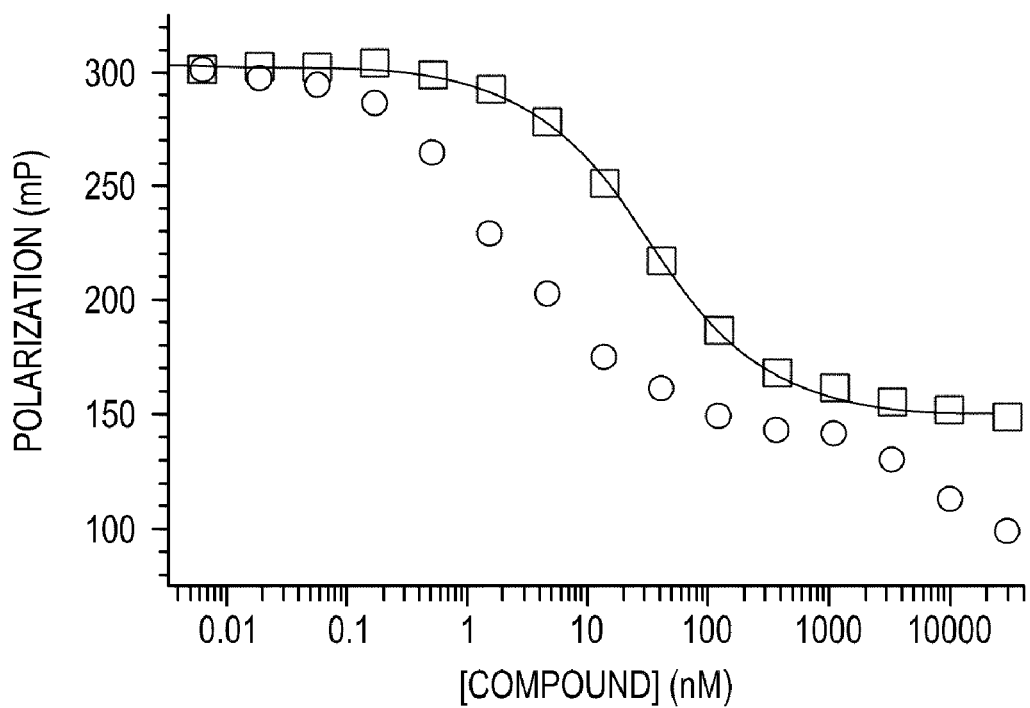
FIG. 4 shows displacement of Predictor™ hERG Tracer Red from hERG-CD8 membranes. (A) Displacement by E-4031 (□) or astemizole (○). (B) Displacement by astemizole in the absence (○) or presence (x) of 30 μM E-4031. Corrected data (●) accounts for the non-specific displacement seen in the presence of E-4031.
Figure 4B:
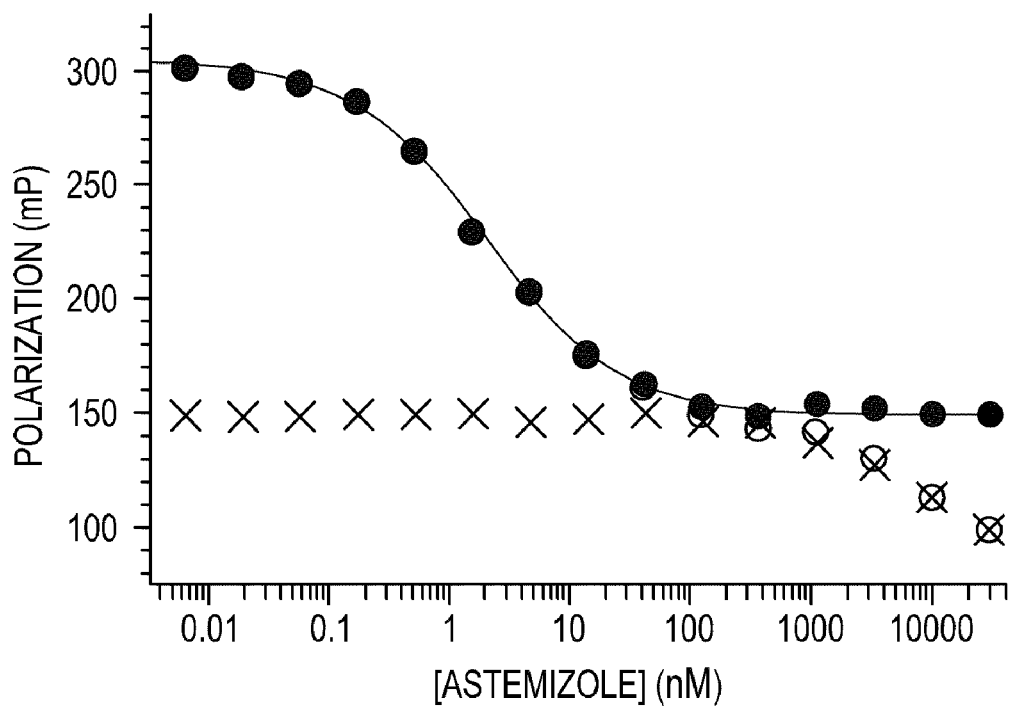

Initial tracer displacement assays using 1 nM Predictor™ hERG Tracer Red and 85 μg (total protein)/mL of CD8_hERG membranes were performed using two well-characterized hERG binding ligands, astemizole and E-4031, which have been shown to bind to hERG with $K_i$ values in the low single- to low double-digit nM range, respectively (see, Finlayson, K.; Turnbull, L.; January, C. T.; Sharkey, J.; Kelly, J. S., [3H]dofetilide binding to HERG transfected membranes: a potential high throughput preclinical screen. *Eur J Pharmacol* 2001, 430, (1), 147-8; Chiu, P. J.; Marcoe, K. F.; Bounds, S. E.; Lin, C. H.; Feng, J. J.; Lin, A.; Cheng, F. C.; Crumb, W. J.; Mitchell, R., Validation of a [3H]astemizole binding assay in HEK293 cells expressing HERG K+ channels. *J Pharmacol Sci* 2004, 95, (3), 311-9; and Finlayson, K.; Pennington, A. J.; Kelly, J. S., [3H]dofetilide binding in SHSY5Y and HEK293 cells expressing a HERG-like K+ channel? *Eur J Pharmacol* 2001, 412, (3), 203-12). Displacement with E-4031 produced data consistent with a one-site competition model, and an $IC_{50}$ value of 11 nM (FIG. 4). Displacement by astemizole, however produced data that appeared to be consistent with a two-site binding model, with binding of the tracer to a second site being displaced only in the presence of high concentrations (>1 μM) of astemizole. When the experiment was repeated using control membranes from the parental 293 cells which lacked overexpressed hERG K+ channels, this same lower-affinity displacement was also seen, suggesting that a non-hERG component in the membrane, or the membrane itself, can bind the tracer, and that this interaction can be displaced by certain compounds. To correct for this non-hERG binding component, displacement of tracer by astemizole was repeated in the presence or absence of 30 μM E-4031, which is expected to compete all hERG-specific binding of the tracer. When the data were corrected by removing the non-hERG component of the displacement curve (FIG. 4, panel B), an $IC_{50}$ value of 2.7 nM as obtained. As a simpler alternative to performing the astemizole displacement assay in the presence or absence of E-4031, displacement data that provided a polarization value of less than that seen in a control well containing saturating E-4031 could be discarded, and the astemizole data then fit to a curve with the minimum mP value fixed to that seen in the control well contained saturating E-4031.

Figure 5:
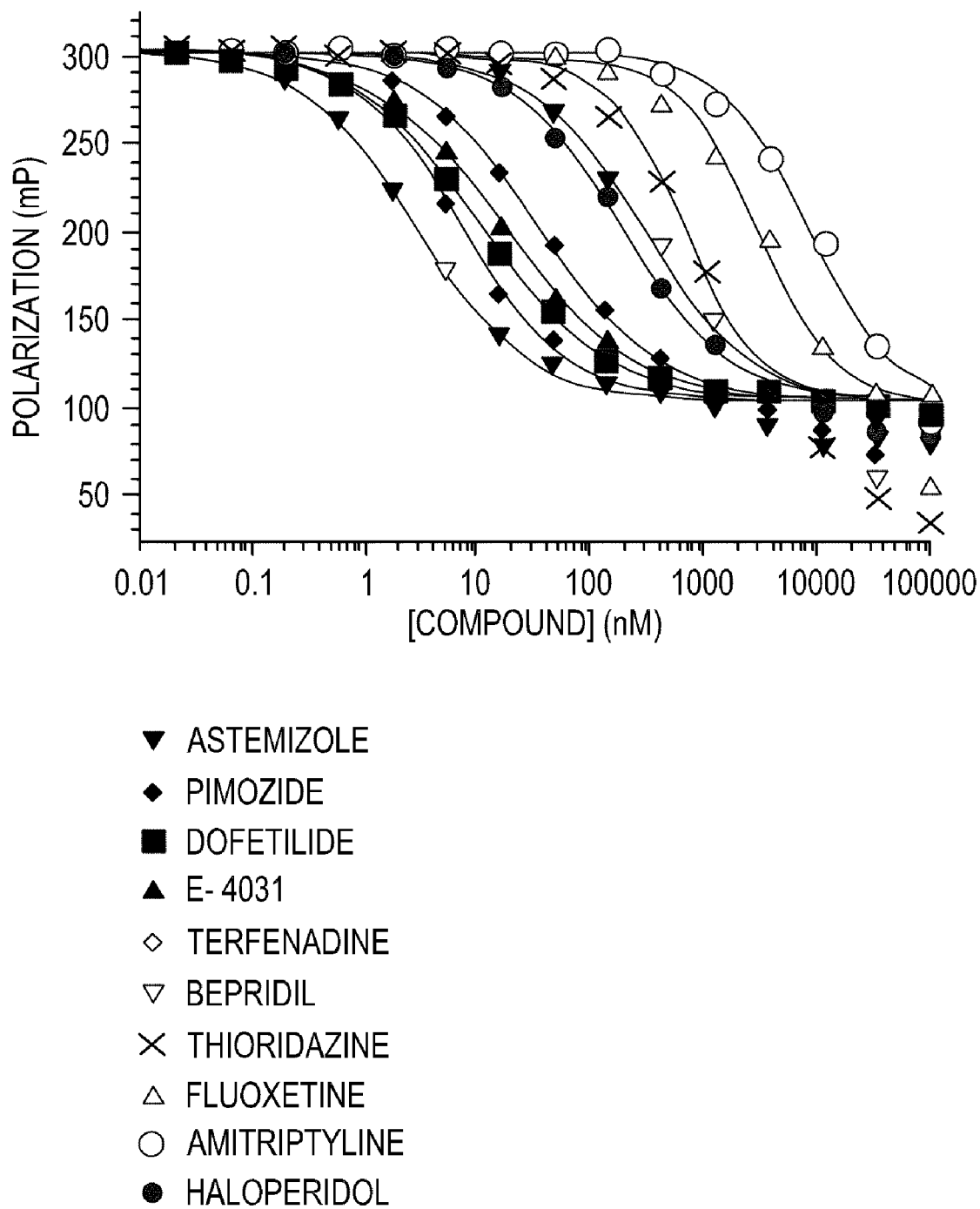
FIG. 5 shows displacement of Predictor™ hERG Tracer Red from CD8-hERG membranes by known hERG K+ channel blockers that span a range of affinities for the hERG K+ channel. Raw data are shown by respective symbols. Solid lines represent displacement curves that have been corrected as described herein.
Figure 6A:
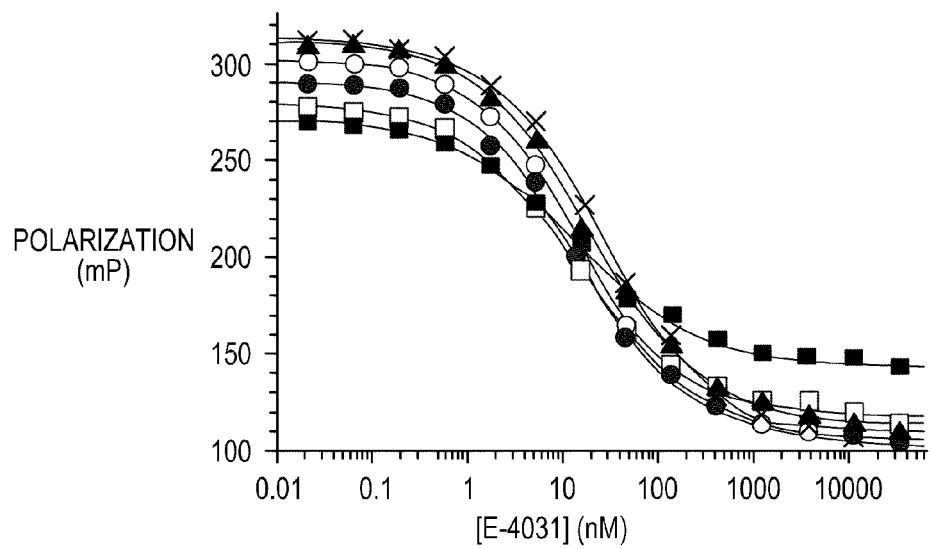
FIG. 6(A) shows a time course study to determine signal stability (polarization shift and IC$_{50}$ value) and assay robustness (Z' value) over time. The assay plate was read (■) 30 minutes, (□) 1 hour, (●) 2 hours, (○) 4 hours, (▲) 6 hours, (x) 24 hours after addition of tracer and membrane to a dilution series of E-4031. Each datapoint represents the average of duplicate measurements, except the 30 μM E-4031 datapoint which contains 28 replicates in order to calculate Z' values (Table 2). Error bars are shown but in general are smaller than the symbol used to mark the datapoint.
Figure 6B:
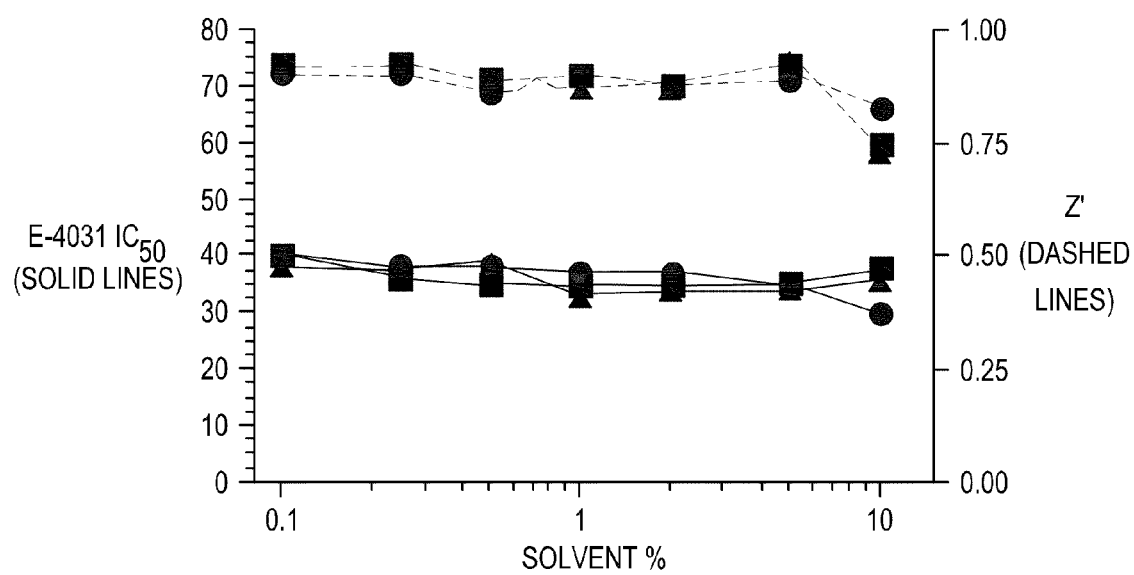
In FIG. 6(B), the assay was repeated in the presence of various concentrations of DMSO (■), methanol (●), or ethanol (▲) and read after 2 hours, IC$_{50}$ values are connected by solid lines, Z' values are connected by dashed lines.

The FP assay using Predictor™ hERG Tracer Red was then validated against a series of compounds that are known to block the hERG K⁺ channel across a wide range of affinities, with nM to μM $K_i$ or $IC_{50}$ values reported in the literature (FIG. 5). Like astemizole, several compounds were able to displace the non-hERG binding component of the tracer at high compound concentrations, but this was easily corrected and there was excellent correlation between the corrected $IC_{50}$ values and values that had been reported in the literature (Table 2). We then evaluated signal stability ($IC_{50}$ value) and assay robustness (determination of Z' value; see, Zhang, J. H.; Chung, T. D.; Oldenberg, K. R., A simple statistical parameter for use in evaluation and validation of high throughput screening assays. *J Biomol Screen* 1999, 4, 67-73) at different time points after the addition of all assay components. As shown in FIG. 6 and Table 3, the assay reports an $IC_{50}$ value that varies by less than 25% between 30 minutes and 6 hours, and then increases slightly (approximately 2-fold) within 24 hours. Although the total polarization shift continued to increase over the course of this experiment, Z' values were excellent ($\geq 0.87$) at all time points examined. Additionally, when the assay was repeated in the presence of increasing concentrations of DMSO, ethanol, or methanol (to determine assay tolerance to solvents that are commonly used for compound storage), negligible effect was seen on either Z' or E-4031 $IC_{50}$ values at up to 10% solvent (FIG. 6, panel B). In separate experiments, the assay was seen to provide data of similar quality using polypropylene plates (Matrical MP101-1-PP), but performance was slightly compromised when using NBS-coated polystyrene plates (Corning 3676).

TABLE 2

Comparison of $IC_{50}$ values (in nM) as reported by patch-clamp or radioligand displacement assays, and in the FP assay described herein.

| Compound | Patch clamp | Radioligand | FP |
| --- | --- | --- | --- |
| Astemizole | 1 | 1-7 | 2.7 |
| Pimozide | 18 | 3-80 | 7.2 |
| Dofetilide | 12-15 | 6-40 | 11 |
| E-4031 | 8-48 | 20-80 | 17 |
| Terfenadine | 16-204 | 30-110 | 33 |
| Haloperidol | 28-174 | 90-180 | 187 |
| Bepridil | 550 | 170-450 | 279 |
| Thioridazine | 36-1250 | 737-1710 | 655 |
| Fluoxetine | 990 | 1920-3040 | 2880 |
| Amitriptyline | 10,000 | 2440 | 8135 |

Literature values for radioligand displacement or patch-clamp assays are found in Diaz, G. J.; Daniell, K.; Leitza, S. T.; Martin, R. L.; Su, Z.; McDermott, J. S.; Cox, B. F.; Gintant, G. A., The [3H]dofetilide binding assay is a predictive screening tool for hERG blockade and proarrhythmia: Comparison of intact cell and membrane preparations and effects of altering [K+]o. J Pharmacol Toxicol Methods 2004, 50, (3), 187-99; Deacon, M.; Singleton, D.; Szalkai, N.; Pasieczny, R.; Peacock, C.; Price, D.; Boyd, J.; Boyd, H.; Steidl-Nichols, J. V.; Williams, C., Early evaluation of compound QT prolongation effects: a predictive 384-well fluorescence polarization binding assay for measuring hERG blockade. J Pharmacol Toxicol Methods 2007, 55, (3), 238-47; and Wible, B. A.; Hawryluk, P.; Ficker, E.; Kuryshev, Y. A.; Kirsch, G.; Brown, A. M., HERG-Lite: a novel comprehensive high-throughput screen for drug-induced hERG risk. J Pharmacol Toxicol Methods 2005, 52, (1), 136-145.

TABLE 3

Assay signal stability and robustness over time for the FP assay described herein.

| Time | $IC_{50}$ (nM) | Delta-mP | Z' |
| --- | --- | --- | --- |
| 30 Minutes | 14 | 107 | .87 |
| 1 hour | 13 | 146 | .90 |
| 2 hours | 14 | 173 | .91 |
| 4 hours | 16 | 191 | .92 |
| 6 hours | 19 | 194 | .93 |
| 24 hours | 29 | 210 | .94 |

$IC_{50}$ value is for E-4031; Z' values were calculated from 28 replicate well containing either DMSO (control) or 30 μM E-4031.

The FP assay results using astemizole to displace the tracer suggest the presence of a second, lower-affinity binding site in membranes prepared from the high-expression hERG cell line described herein and in non-transfected 293 cells. A second, lower-affinity binding site for dofetilide (see, Finlayson, K.; Turnbull, L.; January, C. T.; Sharkey, J.; Kelly, J. S., [3H]dofetilide binding to HERG transfected membranes: a potential high throughput preclinical screen. *Eur J Pharmacol* 2001, 430, (1), 147-8) or astemizole (see, Chiu, P. J.; Marcoe, K. F.; Bounds, S. E.; Lin, C. H.; Feng, J. J.; Lin, A.; Cheng, F. C.; Crumb, W. J.; Mitchell, R., Validation of a [3H]astemizole binding assay in HEK293 cells expressing HERG K⁺ channels. *J Pharmacol Sci* 2004, 95, (3), 311-9) has previously been identified in radioligand binding studies. These sites remain uncharacterized in radioligand studies yet do not prevent accurate determination of hERG affinity for test compounds. Described herein for the hERG K⁺ channel of the present invention are two straightforward procedures to correct data from test compounds that show apparent inhibition beyond that seen in the presence of 30 μM E-4031.

Although the ultimate measure of predictability of any hERG in vitro assay is often taken to be correlation with prolongation of the Q-T interval in animal models (see, Lynch, J. J., Jr.; Wallace, A. A.; Stupienski, R. F., 3rd; Baskin, E. P.; Beare, C. M.; Appleby, S. D.; Salata, J. J.; Jurkiewicz, N. K.; Sanguinetti, M. C.; Stein, R. B.; et al., Cardiac electrophysiologic and antiarrhythmic actions of two long-acting spirobenzopyran piperidine class III agents, L-702,958 and L-706,000 [MK-499]. *J Pharmacol Exp Ther* 1994, 269, (2), 541-54; and Gintant, G. A.; Su, Z.; Martin, R. L.; Cox, B. F., Utility of hERG assays as surrogate markers of delayed cardiac repolarization and QT safety. *Toxicol Pathol* 2006, 34, (1), 81-90), the hERG K⁺ channel assay described herein achieves the penultimate result, namely, an excellent correlation with literature data on patch-clamp $IC_{50}$ values for compounds with a documented ability to block hERG currents. The assay agrees with literature patch-clamp $IC_{50}$ values with no more than a 3-fold discrepancy across the patch-clamp data set, and when the FP results are compared across both patch-clamp and radioligand binding data, the FP data falls within the ranges reported by these techniques. The assay is fully homogenous, uses a red-shifted tracer to lessen problems of compound interference, and has a Z' value of >0.8 over at least a 24-hour assay read window. Although we observed that some compounds produce a greater displacement of the FP signal than does the standard, E-4031, this signal is not hERG-dependent and can be easily identified and corrected for during $IC_{50}$ profiling. Together, these features make the assay well suited to routine and even automated compound profiling.

Each of the above-cited references, as well as U.S. Pat. No. 5,206,240 and all synthetic methods disclosed therein, are hereby incorporated by reference as if set forth fully herein.

The invention claimed is:

1. An assay for screening a test compound, wherein said assay is a binding assay using a fluorescent tracer and a source of a hERG K$^+$ channel or fragment thereof, comprising:
   a) incubating an assay sample comprising the fluorescent tracer, the source of the hERG K$^+$ channel or fragment thereof, an assay buffer, and a test compound; and
   b) measuring the amount of the fluorescent tracer bound to the hERG K$^+$ channel or fragment thereof in the sample, wherein the fluorescent tracer is a compound of structural formula:

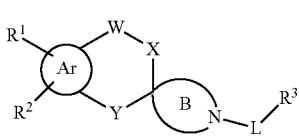

(I)

or a pharmaceutically acceptable salt thereof, wherein:
Ar is a benzo ring;
R$^1$ and R$^2$ are independently hydrogen or —NHSO$_2$CH$_3$;
the ring system comprising W, X, and Y 6-membered ring system wherein Y is —O—, W is C═O, —CH$_2$—, C═NOH, —NH—, CHNH$_2$, ═CH—, or ═N—, and X is —CH$_2$— or ═CH—;
B is a 6-membered N-containing ring;
L is —(CR$^4$R$^5$)$_m$-Q—(CR$^4$R$^5$)$_q$—NH—[CZ—(CR$^4$R$^5$)$_u$-(D)$_w$]$_z$—, wherein
R$^4$ and R$^5$ are independently hydrogen or C$_{1-6}$ alkyl,
Q is a bond, —O—, C═O, CHOH, —NR$^5$— or —S(O)$_n$—,
Z is ═O or ═S,
D is —O—, —S(O)$_n$—, —NR$^5$—, or —NR$^5$SO$_2$—,
m and q are independently 1 to about 5,
n is 0, 1, or 2,
u is 0 to about 7,
w is 0 or 1,
z is 1 or 2; and
R$^3$ is a fluorescent dye.

2. The assay of claim 1, wherein screening the test compound provides an indication as to the propensity thereof to prolong the Q-T interval in a human electrocardiogram and thereby induce cardiotoxicity or cardiac arrhythmia in a human subject.

3. The assay of claim 1, wherein the incubating is in the presence of (i) different amounts of the test compound in separate assay samples or (ii) a mixture of test compounds in the assay sample.

4. The assay of claim 1, wherein the assay buffer is a HEPES-based buffer containing KCl, MgCl$_2$, and PLURONIC F-127.

5. The assay of claim 4, wherein the assay buffer comprises 15 mM to 50 mM HEPES, 5 mM to 20 mM KCl, 0.5 mM to 2 mM MgCl$_2$, and 0.02% to about 0.1% PLURONIC F-127.

6. The assay of claim 5, wherein the assay buffer comprises 25 mM HEPES, 15 mM KCl, 1 mM MgCl$_2$, and 0.05% PLURONIC F-127.

7. The assay of claim 6, wherein the assay buffer is at a pH between pH 7.2 and pH 7.6 at room temperature.

8. The assay of claim 7, wherein the assay buffer is at pH 7.4.

9. The assay of claim 1, wherein the measuring of tracer bound in (b) is by fluorescence polarization.

10. The assay of claim 3, wherein step b) further comprises:
   i) determining specifically bound fluorescent tracer for each sample; and
   ii) calculating the inhibition of fluorescent tracer binding by the test compound or mixture of test compounds.

11. The assay of claim 1, wherein the source of the hERG K⁺ channel or fragment thereof is selected from the group consisting of:
   i) membrane preparations derived from cells expressing on the surface thereof the hERG K⁺ channel of fragment thereof;
   ii) cells expressing on the surface thereof the hERG K⁺ channel of fragment thereof; and
   iii) membrane preparations derived from tissue expressing on the surface thereof the hERG K⁺ channel of fragment thereof.

12. The assay of claim 11, wherein the source of the hERG K⁺ channel or fragment thereof are membrane preparations derived from cells expressing on the surface thereof the hERG K⁺ channel or fragment thereof.

13. The assay of claim 12, wherein the cells express at least about 100 pmol of hERG K⁺ channel per mg of total membrane protein.

14. The assay of claim 12, wherein the cells express a hERG K⁺ channel for which the hERG current as determined by patch clamping with a fully automated high throughput patch clamp system is in a range of about 1500 pA to about 2500 pA.

15. The assay of claim 12, wherein the cells are HEK 293 cells or CHO cells.

16. The assay of claim 12, wherein the cells have been transfected with an expression vector selected from the group consisting of:
   i) an isolated and purified nucleic acid comprising a nucleotide sequence which encodes a hERG K⁺ channel having an amino acid sequence that is at least 80% homologous to that of SEQ ID NO: 1 or a fragment thereof; and
   ii) an isolated and purified nucleic acid comprising a nucleotide sequence which encodes a hERG K⁺ channel having the amino acid sequence of SEQ ID NO: 1 or a fragment thereof.

17. The assay of claim 16, wherein the nucleic acid further comprises a nucleotide sequence which encodes an internal ribosomal entry site protein and a nucleotide sequence which encodes CD-8 plasma membrane protein.

18. The assay of claim 17, wherein the nucleotide sequences which encode the internal ribosomal entry site protein and the CD-8 plasma membrane protein are located successively downstream from the nucleotide sequence which encodes the hERG K⁺ channel.

19. The assay of claim 18, wherein expression of the hERG K⁺ channel is coupled to expression of the CD-8 plasma protein by means of the nucleotide sequence which encodes an internal ribosomal entry site protein.

20. A kit for screening test compounds, said kit comprising:
   a) a fluorescent tracer or a pharmaceutically acceptable salt thereof;
   b) a source of the hERG K⁺ channel or fragment thereof; and
   c) an assay buffer wherein the fluorescent tracer is a compound of structural formula:

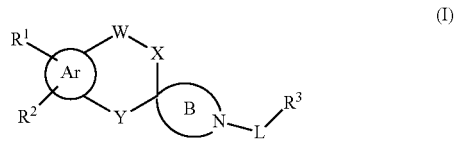

wherein:
Ar is a benzo ring;
$R^1$ and $R^2$ are independently hydrogen or —NHSO$_2$CH$_3$;
the ring system comprising W, X, and Y is a 6-membered ring system wherein Y is —O—,
  W is C=O, —CH$_2$—, C=NOH, —NH—, CHNH$_2$, =CH—, or =N—, and X is —CH$_2$— or =CH—;
B is a 6-membered N-containing ring;
L is —(CR$^4$R$^5$)$_m$-Q-(CR$^4$R$^5$)$_q$—NH—[CZ—(CR$^4$R$^5$)$_u$-(D)$_w$]$_z$-, wherein
  $R^4$ and $R^5$ are independently hydrogen or C$_{1-6}$ alkyl,
  Q is a bond, —O—, C=O, CHOH, —NR$^5$— or —S(O)$_n$—,
  Z is =O or =S,
  D is —O—, —S(O)$_n$—, —NR$^5$—, or —NR$^5$SO$_2$—,
  m and q are independently 1 to about 5,
  n is 0, 1, or 2,
  u is 0 to about 7,
  w is 0 or 1,
  z is 1 or 2; and
$R^3$ is a fluorescent dye.

21. The kit of claim 20, wherein the source of the hERG K⁺ channel or fragment thereof are membrane preparations derived from cells expressing on the surface thereof the hERG K⁺ channel or fragment thereof.

22. The kit of claim 21, wherein the cells express at least about 100 pmol of hERG K⁺ channel per mg of total membrane protein.

23. The kit of claim 21, wherein the cells express a hERG K⁺ channel for which the hERG current as determined by patch clamping with a fully automated high throughput patch clamp system is in a range of about 1500 pA to about 2500 pA.

24. The kit of claim 21, wherein the cells are HEK 293 cells or CHO cells.

25. The kit of claim 21, wherein the cells have been transfected with an expression vector having the nucleotide sequence of SEQ ID NO: 2.

26. The kit of claim 25, wherein expression of the hERG K⁺ channel is coupled to expression of CD-8 plasma protein by means of a nucleotide sequence which encodes an internal ribosomal entry site protein.

27. The kit of claim 20, wherein the assay buffer comprises 25 mM HEPES, 15 mM KCl, 1 mM MgCl$_2$, and 0.05% PLURONIC F-127.

28. The kit of claim 27, wherein the assay buffer is at a pH between pH 7.2 and pH 7.6 at room temperature.

29. The kit of claim 28, wherein the assay buffer is at pH 7.4.

30. The assay of claim 1, further comprising:
   c) comparing the amount of tracer bound in the sample with the amount of tracer bound in the absence of the test compound, and determining whether the test compound has an effect on the tracer binding by identifying a comparative difference in the amount of tracer bound in the presence and absence of the test compound.

31. The assay of claim 1, wherein L is —$(CR^4R^5)_m$-Q-$(CR^4R^5)_q$—NH—$[CZ]_z$—.

32. The assay of claim 31, wherein L is —$(CH_2)_m$—O—$(CH_2)_q$—NH—C=O—.

33. The kit of claim 20, wherein L is —$(CR^4R^5)_m$-Q-$(CR^4R^5)_q$—NH—$[CZ]_z$—.

34. The assay of claim 33, wherein L is —$(CH_2)_m$—O—$(CH_2)_q$—NH—C=O—.

* * * * *

UNITED STATES PATENT AND TRADEMARK OFFICE
CERTIFICATE OF CORRECTION

PATENT NO. : 8,133,695 B2
APPLICATION NO. : 12/394605
DATED : March 13, 2012
INVENTOR(S) : David Piper et al.

It is certified that error appears in the above-identified patent and that said Letters Patent is hereby corrected as shown below:

Claim 1b), column 55, line 58, "Y 6-membered ring" should read --Y is a 6-membered ring--

Claim 11 i), column 57, line 11, "channel of fragment" should read --channel or fragment--
Claim 11 ii), column 57, line 14, "channel of fragment" should read --channel or fragment--
Claim 11 iii), column 57, line 16, "channel of fragment" should read --channel or fragment--

Claim 34, column 60, line 1, "The assay of claim 33" should read --The kit of claim 33--

Signed and Sealed this
Twenty-eighth Day of August, 2012

David J. Kappos
*Director of the United States Patent and Trademark Office*